US012571033B2

(12) United States Patent
Schneider et al.

(10) Patent No.: US 12,571,033 B2
(45) Date of Patent: Mar. 10, 2026

(54) PURIFYING AND POLYMERIZING 3'-BLOCKED NUCLEOTIDES

(71) Applicants: ILLUMINA, INC., San Diego, CA (US); ILLUMINA CAMBRIDGE LIMITED, Cambridge (GB)

(72) Inventors: Kim Schneider, Cambridge (GB); Jason Betley, Buntingford (GB); Oliver Miller, Linton (GB); Bradley Drews, San Diego, CA (US); Dominic Smith, Cambridge (GB); Rajagopal Panchapakesan, Escondido, CA (US); Patrick McCauley, Linton (GB); Stephen Mason, Cambridge (GB); Tommaso Moschetti, Cambridge (GB); Michael Chesney, San Diego, CA (US); Marta Richardson, Newmarket (GB); Elliot Lawrence, Cambridge (GB); Amanda Jackson, Saffron Walden (GB); Rosamond Jackson, Duxford (GB); Erin Imsand, San Diego, CA (US); Henry Day, Newmarket (GB)

(73) Assignee: ILLUMINA, INC., San Diego, CA (US)

( * ) Notice: Subject to any disclaimer, the term of this patent is extended or adjusted under 35 U.S.C. 154(b) by 939 days.

(21) Appl. No.: 17/748,973

(22) Filed: May 19, 2022

(65) Prior Publication Data

US 2022/0389500 A1 Dec. 8, 2022

Related U.S. Application Data

(60) Provisional application No. 63/193,413, filed on May 26, 2021.

(51) Int. Cl.

| | |
|---|---|
| ***C12Q 1/68*** | (2018.01) |
| ***C12N 9/12*** | (2006.01) |
| ***C12Q 1/6869*** | (2018.01) |

(52) U.S. Cl.
CPC ......... *C12Q 1/6869* (2013.01); *C12N 9/1252* (2013.01); *C12Y 207/07007* (2013.01)

(58) Field of Classification Search
CPC .............................. C12Q 1/6869; C12Q 1/686
See application file for complete search history.

(56) References Cited

U.S. PATENT DOCUMENTS 4,739,634 A 4/1988 Watanabe

FOREIGN PATENT DOCUMENTS

| | | |
|---|---|---|
| WO | 2014/139596 A1 | 9/2014 |
| WO | 2016/020691 A1 | 2/2016 |
| WO | 2020/120179 A1 | 6/2020 |
| WO | 2020/165137 A1 | 8/2020 |

OTHER PUBLICATIONS

Velic et al. "Supramolecular inclusion complexes between a coumarin dye and β-cyclodextrin, and attachment kinetics of thiolated β-cyclodetrin to gold surface"; Journal of Molecular Structure; 598; pp. 49-56 (2001).
Moritz et al. "Spectroscopic studies of β-cyclodextrin-complexed cyaVoline dyes"; Journal of Photochemistry and Photobiology A: Chemistry; 169:3; pp. 211-220 (2004).
Kircher, M.; et al.: "Improved base calling for the Illumina Genome Analyzer using machine learning strategies", Genome Biology 10(8):R83 (Aug. 14, 2009).
International Search Report and Written Opinion for PCT/US2022/030008; 17 pages.

*Primary Examiner* — Jezia Riley
(74) *Attorney, Agent, or Firm* — Sheppard, Mullin, Richter & Hampton LLP; Jaime D. Choi

(57) ABSTRACT

A method for purifying nucleotides is provided, that includes preparing a solution comprising (a) 3'-blocked nucleotides, (b) 3'-OH nucleotides, (c) a polishing polymerase, and (d) a template. The polishing polymerase and the template are used to selectively polymerize the 3'-OH nucleotides and thus reduce a concentration in the solution of the 3'-OH nucleotides relative to the 3'-blocked nucleotides.

22 Claims, 14 Drawing Sheets

Specification includes a Sequence Listing.

PURIFYING AND POLYMERIZING 3'-BLOCKED NUCLEOTIDES

CROSS-REFERENCE TO RELATED APPLICATION

This application claims the benefit of U.S. Provisional Patent Application No. 63/193,413, filed May 26, 2021 and entitled "Purifying and Polymerizing 3'-Blocked Nucleotides," the entire contents of which are incorporated by reference herein.

FIELD

This application relates to methods of purifying nucleotides.

SEQUENCE LISTING

The instant application contains a Sequence Listing which has been submitted electronically in ASCII format and is hereby incorporated by reference in its entirety. Said ASCII copy, created on May 6, 2022, is named 85491.01600.txt and is 3.09 kilobytes in size.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to diseases, and measuring response to various types of treatment. A common technique for detecting specific nucleic acid sequences in a biological sample is nucleic acid sequencing.

Nucleic acid sequencing methodology has evolved from the chemical degradation methods used by Maxam and Gilbert and the strand elongation methods used by Sanger. Several sequencing methodologies are now in use which allow for the parallel processing of thousands of nucleic acids all on a single chip. Some platforms include bead-based and microarray formats in which silica beads are functionalized with probes depending on the application of such formats in applications including sequencing, genotyping, or gene expression profiling.

Some sequencing systems use fluorescence-based detection, whether for "sequencing-by-synthesis" or for genotyping, in which a given nucleotide is labeled with a fluorescent label, and the nucleotide is identified based on detecting the fluorescence from that label.

SUMMARY

Examples provided herein are related to purifying and polymerizing 3'-blocked nucleotides. Methods for performing such purifying and polymerizing, and associated compositions and devices, are disclosed.

In some examples, a method for purifying nucleotides is provided herein. The method may include preparing a solution including (a) 3'-blocked nucleotides, (b) 3'-OH nucleotides, (c) a polishing polymerase, and (d) a template. The method may include using the polishing polymerase and the template to selectively polymerize the 3'-OH nucleotides and thus reduce a concentration in the solution of the 3'-OH nucleotides relative to the 3'-blocked nucleotides.

In some examples, each of the 3'-blocked nucleotides includes a detectable moiety. In some examples, preparing the solution includes adding water, the polishing polymerase, and the template to a lyophilized mixture of the 3'-blocked nucleotides and the 3'-OH nucleotides. In some examples, preparing the solution includes adding water to a lyophilized mixture of the 3'-blocked nucleotides, the 3'-OH nucleotides, the polishing polymerase, and the template.

In some examples, the polishing polymerase includes a thermostable polymerase. In some examples, the thermostable polymerase is selected from the group consisting of: Deep Vent, Taq, Bst, *Sulfolobus* DNA Polymerase IV, and Pfu. In some examples, the method further includes heating the solution while using the thermostable polymerase and the template. In some examples, the solution is heated to a temperature of about 30-75° C. In some examples, the solution is heated to a temperature of about 40-60° C.

In some examples, the solution is heated using a cache manifold including an inner structure, an outer sleeve, and a spiral tube through which the solution flows, wherein at least one of the inner structure and the outer sleeve is heated. In some examples, the inner structure includes an inner sleeve through which a fluid flows.

In some examples, the solution further includes yeast inorganic pyrophosphatase (YPP) to increase a rate at which 3'-OH nucleotides are polymerized as compared to such rate in the absence of YPP.

In some examples, the polishing polymerase and the template are used in a sequencing-by-synthesis instrument.

In some examples, the solution further may include a modified α-cyclodextrin, modified β-cyclodextrin, or modified γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin. In some examples, each of the 3'-blocked nucleotides may be coupled to a fluorescent dye, and the modified α-cyclodextrin, modified β-cyclodextrin, or modified γ-cyclodextrin may promote solubility of the fluorescent dye. In some examples, the modified α-cyclodextrin, modified β-cyclodextrin, or modified γ-cyclodextrin has a concentration in the solution of about 1% to about 10% (weight/volume). In some examples, the 3'-blocked nucleotides have a concentration in the solution of less than about 1.5 mM. In some examples, the solution further includes magnesium ions at a concentration of at least about 1 mM. In some examples, the modified α-cyclodextrin, modified β-cyclodextrin, or modified γ-cyclodextrin may inhibit formation of diphosphate in the solution. In some examples, the modified α-cyclodextrin, modified β-cyclodextrin, or modified γ-cyclodextrin may inhibit formation of tetraphosphate in the solution.

In some examples, a method of polymerizing nucleotides is provided. The method may include reducing a concentration, in a first solution including 3'-blocked nucleotides and 3'-OH nucleotides, of the 3'-OH nucleotides relative to the 3'-blocked nucleotides. The method may include preparing a second solution including (a) the 3'-blocked nucleotides from the first solution, and (b) a sequencing-by-synthesis (SBS) polymerase. The method may include using the SBS polymerase and a first template to polymerize the 3'-blocked nucleotides.

In some examples, reducing the concentration, in the first solution, of the 3'-OH nucleotides relative to the 3'-blocked nucleotides includes selectively polymerizing the 3'-OH nucleotides using a polishing polymerase and a second template. In some examples, the second solution further includes the polishing polymerase. In some examples, the polishing polymerase includes a thermostable polymerase. In some examples, the thermostable polymerase is selected from the group consisting of: Deep Vent, Taq, Bst, *Sulfolobus* DNA Polymerase IV, and Pfu. In some examples, the second solution further includes the polymerized 3'-OH nucleotides. In some examples, the polishing polymerase and the SBS polymerase are used on a sequencing-by-synthesis instrument.

In some examples, preparing the second solution includes adding the SBS polymerase to the first solution after reducing the concentration, in the first solution, of the 3'-OH nucleotides relative to the 3'-blocked nucleotides.

In some examples, the first solution further includes yeast inorganic pyrophosphatase (YPP) to increase a rate at which 3'-OH nucleotides are polymerized as compared to such rate in the absence of YPP.

In some examples, the first and second solutions are heated using a cache manifold including an inner structure, an outer sleeve, and a spiral tube through which the first and second solutions flow at different times, wherein at least one of the inner structure and the outer sleeve is heated. In some examples, the inner structure includes an inner sleeve through which a fluid flows.

In some examples, each of the 3'-blocked nucleotides in the first solution includes a detectable moiety. In some examples, the method further includes detecting the detectable moieties of the 3'-blocked nucleotides while the 3'-blocked nucleotides are being polymerized using the SBS polymerase and the first template.

In some examples, the first solution further may include a modified α-cyclodextrin, modified β-cyclodextrin, or modified γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin. In some examples, each of the 3'-blocked nucleotides may be coupled to a fluorescent dye, and the modified α-cyclodextrin, modified β-cyclodextrin, or modified γ-cyclodextrin may promote solubility of the fluorescent dye. In some examples, the modified α-cyclodextrin, modified β-cyclodextrin, or modified γ-cyclodextrin has a concentration in the first solution of about 1% to about 10% (weight/volume). In some examples, the 3'-blocked nucleotides have a concentration in the first solution of less than about 1.5 mM. In some examples, the first solution further may include magnesium ions at a concentration of at least about 1 mM. In some examples, the modified α-cyclodextrin, modified β-cyclodextrin, or modified γ-cyclodextrin may inhibit formation of diphosphate in the first solution. In some examples, the modified α-cyclodextrin, modified β-cyclodextrin, or modified γ-cyclodextrin may inhibit formation of tetraphosphate in the first solution. In some examples, the second solution further may include the modified α-cyclodextrin, modified β-cyclodextrin, or modified γ-cyclodextrin.

In some examples, a solution is provided herein. The solution includes water; 3'-blocked nucleotides; 3'-OH nucleotides; a polishing polymerase; and a template. The 3'-OH nucleotides may be selectively polymerizable using the polishing polymerase and the template.

In some examples, each of the 3'-blocked nucleotides includes a detectable moiety. In some examples, the polishing polymerase includes a thermostable polymerase. In some examples, the thermostable polymerase is selected from the group consisting of: Deep Vent, Taq, Bst, *Sulfolobus* DNA Polymerase IV, and Pfu. In some examples, the solution includes yeast inorganic pyrophosphatase (YPP).

In some examples, the solution further may include a modified α-cyclodextrin, modified β-cyclodextrin, or modified γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin. In some examples, each of the 3'-blocked nucleotides may be coupled to a fluorescent dye, and the modified α-cyclodextrin, modified β-cyclodextrin, or modified γ-cyclodextrin may promote solubility of the fluorescent dye. In some examples, the modified α-cyclodextrin, modified β-cyclodextrin, or modified γ-cyclodextrin has a concentration in the solution of about 1% to about 10% (weight/volume). In some examples, the 3'-blocked nucleotides have a concentration in the solution of less than about 1.5 mM. In some examples, the solution further includes magnesium ions at a concentration of at least about 1 mM. In some examples, the modified α-cyclodextrin, modified β-cyclodextrin, or modified γ-cyclodextrin may inhibit formation of diphosphate in the solution. In some examples, the modified α-cyclodextrin, modified β-cyclodextrin, or modified γ-cyclodextrin may inhibit formation of tetraphosphate in the solution.

In some examples, another solution is provided herein. The solution includes water; 3'-blocked nucleotides; polymerized 3'-OH nucleotides hybridized to a first template; a polishing polymerase; and a sequencing-by-synthesis (SBS) polymerase. The 3'-blocked nucleotides are polymerizable using the SBS polymerase and a second template.

In some examples, each of the 3'-blocked nucleotides includes a detectable moiety. In some examples, the solution includes a modified α-cyclodextrin, modified β-cyclodextrin, or modified, γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin.

In some examples, a lyophilized mixture is provided herein. The lyophilized mixture may include 3'-blocked nucleotides; 3'-OH nucleotides; a polishing polymerase; and a template. When the lyophilized mixture is rehydrated, the 3'-OH nucleotides may be selectively polymerizable using the polishing polymerase and the template.

In some examples, each of the 3'-blocked nucleotides includes a detectable moiety. In some examples, the polishing polymerase includes a thermostable polymerase. In some examples, the thermostable polymerase is selected from the group consisting of: Deep Vent, Taq, Bst, *Sulfolobus* DNA Polymerase IV, and Pfu. In some examples, the lyophilized mixture further includes yeast inorganic pyrophosphatase (YPP). In some examples, the lyophilized mixture includes a modified α-cyclodextrin, modified β-cyclodextrin, or modified γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1A:
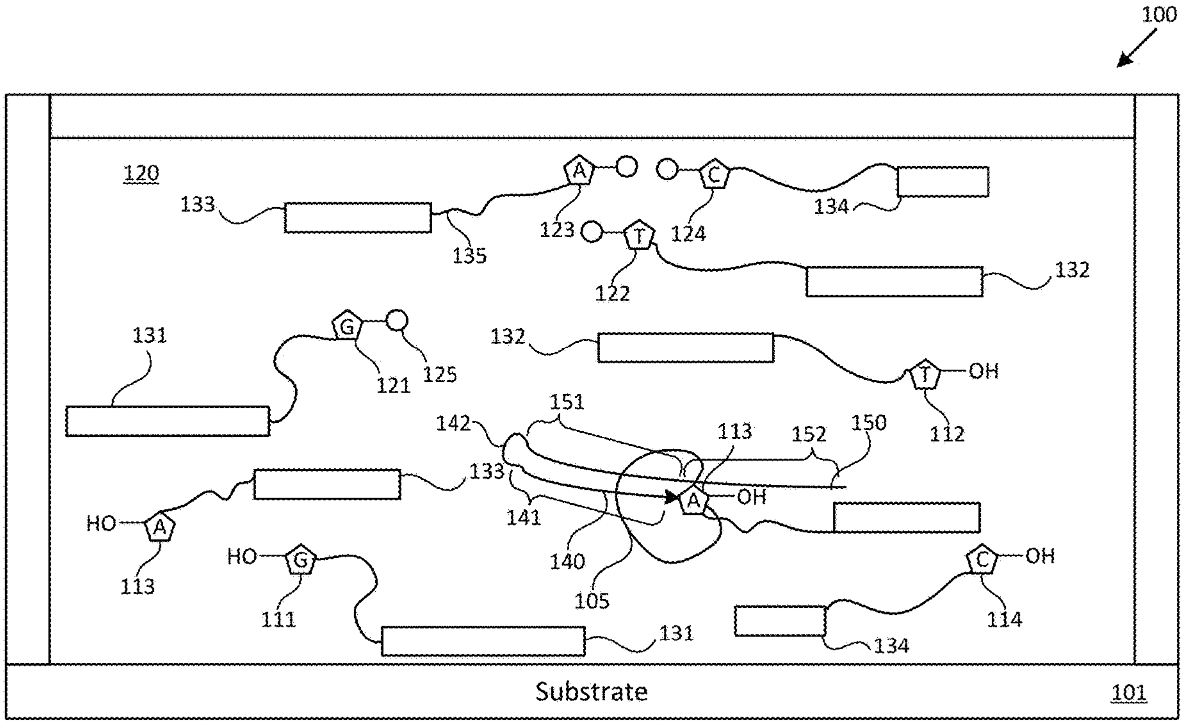
FIGS. 1A-1B schematically illustrate example compositions and operations in a process flow for purifying 3'-blocked nucleotides.

Purifying and polymerizing 3'-blocked nucleotides is provided herein.

For example, the present application relates to purifying, or "polishing," 3'-blocked nucleotides so as to remove any unblocked (3'-OH) nucleotides from solution before beginning sequencing-by-synthesis (SBS) or genotyping operations. For example, the 3'-blocked nucleotides may include a blocking group, e.g., an azidomethyl group, coupled to the nucleotide at the 3' position. The nucleotides also may be coupled to a detectable moiety, such as a fluorophore. When an SBS polymerase polymerizes the 3'-blocked nucleotides by adding a given one of the nucleotides to a growing polynucleotide using a complementary polynucleotide (e.g., a template to be sequenced), that nucleotide may be detected and identified using the detectable moiety, thus allowing the complementary nucleotide to be identified. However, the polymerase may be unable to add another nucleotide to the growing polynucleotide until the 3'-blocking group is removed using a suitable reagent. After the 3'-blocking group is removed, the detectable moiety may be cleaved from that nucleotide and add another 3'-blocked nucleotide to the growing polynucleotide. Such a process may be repeated any suitable number of times, e.g., so as to identify one or more bases in the sequence of the complementary polynucleotide. The detectable moieties of the various 3'-blocked nucleotides may be detected via suitable detection circuitry. In some examples, detectable moieties may include fluorophores that may be detected via suitable optical detection circuitry. However, it will be appreciated that a detectable moiety may be detected in any suitable manner and is not limited to detection via fluorescence.

The presence of 3'-unblocked nucleotides (nucleotides that are not 3'-blocked) may interfere with sequencing the complementary polynucleotide. For example, storage or shipping may cause 3'-blocked nucleotides to become deblocked by hydrolyzing bonds coupling the detectable moieties to the nucleotides, thus converting 3'-blocked nucleotides to 3'-OH nucleotides. Such hydrolysis may be reduced by lyophilizing the 3'-blocked nucleotides prior to storage or shipping, but nonetheless some 3'-OH nucleotides may become mixed with the 3'-blocked nucleotides by the time the nucleotides are to be used. Additionally, or alternatively, when the 3'-blocking groups are initially added during synthesis of the 3'-blocked nucleotides, the reaction yield may not necessarily be 100%, and as such some residual 3'-OH nucleotides may be mixed with the 3'-blocked nucleotides. If 3'-OH nucleotides are mixed with 3'-blocked nucleotides during polymerization, e.g., using an SBS polymerase and a complementary polynucleotide, the 3'-OH nucleotides may cause errors in sequencing the complementary polynucleotide. For example, the SBS polymerase may occasionally add 3'-OH nucleotides to the growing polynucleotide, but because such 3'-OH nucleotides lack a 3'-blocking group, the SBS polymerase may rapidly add another nucleotide to the growing polynucleotide rather than having to wait for addition of a reagent to remove the blocking group. As such, the 3'-OH nucleotides may speed up the polymerization (such speeding up also being called "prephasing"), in which the increased speed may inhibit the detection circuitry from being able to accurately detect and identify the detectable moieties coupled to the 3'-OH nucleotides. As such, the sequence of the complementary polynucleotide may not be fully or accurately determined.

Provided herein are methods for purifying and polymerizing 3'-blocked nucleotides. As described in greater detail below, a concentration of 3'-OH nucleotides may be reduced relative to 3'-blocked nucleotides by selectively polymerizing the 3'-OH nucleotides. Illustratively, a polishing polymerase and a polynucleotide (template) are mixed in an aqueous solution with a mixture of 3'-blocked nucleotides and 3'-OH nucleotides. Unlike SBS polymerases which may polymerize both 3'-blocked nucleotides and 3'-OH nucleotides relatively well, the polishing polymerase may polymerize 3'-OH nucleotides relatively well but may polymerize 3'-blocked nucleotides at a significantly lower rate than the 3'-OH nucleotides. A nonlimiting example of a polishing polymerase is a thermostable polymerase, although there are many other examples of polymerases that polymerize 3'-OH nucleotides at a significantly higher rate than 3'-blocked nucleotides or substantially may not polymerize 3'-blocked nucleotides, e.g., that have not been specifically engineered for use in SBS. The polishing polymerase may polymerize 3'-OH nucleotides in the mixture, removing those nucleotides from solution, while the 3'-blocked nucleotides may remain in solution. An SBS polymerase then may be used to polymerize the 3'-blocked nucleotides, e.g., in an SBS or genotyping process, with reduced interference from 3'-OH nucleotides.

In some examples, the 3'-blocked nucleotides may be purified on the same instrument that performs the subsequent polymerization operation. For example, purifying and polymerizing the 3'-blocked nucleotides both may be performed on the same SBS instrument. As described in greater detail below, the instrument may include a device such as a "cache manifold" that may be used to heat or cool the solution for the purifying, e.g., so that the polishing polymerase may be used at a suitable temperature, and to heat or cool the solution for the polymerizing, e.g., so that the SBS polymerase may be used at a suitable temperature. The cache manifold may include a heat exchanger with inner and outer sleeves, one or both of which may be heated or cooled, and a coiled fluidic pathway that is located between the sleeves and through which the solution to be heated or cooled may flow.

Some terms used herein will be briefly explained. Then, some example systems and example methods for purifying and polymerizing 3'-blocked nucleotides, and associated compositions and devices, will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially", "approximately", and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, the term "nucleotide" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar and/or phosphate moiety compared to naturally occurring nucleotides. Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA or double stranded RNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides can include non-naturally occurring DNA, such as enantiomeric DNA. The precise sequence of nucleotides in a polynucleotide can be known or unknown. The following are example examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "polynucleotide" and "nucleic acid" may be used interchangeably, and can refer to a polymeric form of nucleotides of any length, such as either ribonucleotides or deoxyribonucleotides. Thus, this term includes single-, double-, or multi-stranded DNA or RNA. The term polynucleotide also refers to both double and single-stranded molecules. Examples of polynucleotides include a gene or gene fragment, genomic DNA, genomic DNA fragment, exon, intron, messenger RNA (mRNA), transfer RNA, ribosomal RNA, non-coding RNA (ncRNA) such as PIWI-interacting RNA (piRNA), small interfering RNA (siRNA), and long non-coding RNA (lncRNA), small hairpin (shRNA), small nuclear RNA (snRNA), micro RNA (miRNA), small nucleolar RNA (snoRNA) and viral RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can include modified nucleotides, such as methylated nucleotides and nucleotide analogs including nucleotides with non-natural bases, nucleotides with modified natural bases such as aza- or deaza-purines. In some examples, a polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term 'sequence' refers to the alphabetical representation of a polynucleotide or any nucleic acid molecule, including natural and non-natural bases.

As used herein, "target nucleic acid" or grammatical equivalent thereof can refer to nucleic acid molecules or sequences that it is desired to identify, sequence, analyze and/or further manipulate. In some examples, a target nucleic acid can include a single nucleotide polymorphism (SNP) to be identified. In some examples, a SNP can be identified by hybridizing a probe to the target nucleic acid, and extending the probe. In some examples, the extended probe can be detected by hybridizing the extended probe to a capture probe.

As used herein, "hybridize" is intended to mean noncovalently attaching a first polynucleotide to a second polynucleotide along the lengths of those polynucleotides via specific hydrogen bonding pairing of nucleotide bases. The strength of the attachment between the first and second polynucleotides increases with the length and complementarity between the sequences of monomer units within those polymers. For example, the strength of the attachment between a first polynucleotide and a second polynucleotide increases with the complementarity between the sequences of nucleotides within those polynucleotides, and with the length of that complementarity. By "temporarily hybridized" it is meant that polymer sequences are hybridized to each other at a first time, and dehybridized from one another at a second time.

For example, as used herein, "hybridization," "hybridizing" or grammatical equivalent thereof, can refer to a reaction in which one or more polynucleotides react to form a complex that is formed at least in part via hydrogen bonding between the bases of the nucleotide residues. The hydrogen bonding can occur by Watson-Crick base pairing, Hoogstein binding, or in any other sequence-specific manner. The complex can have two strands forming a duplex structure, three or more strands forming a multi-stranded complex, a single self-hybridizing strand, or any combination of thereof. The strands can also be cross-linked or otherwise joined by forces in addition to hydrogen bonding.

As used herein, a "polymerase" is intended to mean an enzyme having an active site that assembles polynucleotides by polymerizing nucleotides into polynucleotides. A polymerase can bind double stranded DNA and can sequentially add nucleotides to the 3' end of the strand in extension to form a growing polynucleotide having a sequence that is complementary to that of the template.

A "sequencing-by-synthesis polymerase" or "SBS polymerase" is intended to mean an enzyme that polymerizes at least 3'-blocked nucleotides into polynucleotides. If 3'-OH nucleotides are mixed with the 3'-blocked nucleotides, an SBS polymerase also may polymerize such 3'-OH nucleotides. Examples of SBS polymerases include Enterobacterial phage ϕ29 DNA polymerase and *Bacillus subtilis* DNA polymerase I (Bsu) which may be engineered to polymerize 3'-blocked nucleotides.

A "polishing polymerase" is intended to mean an enzyme that polymerizes 3'-OH nucleotides, for example by adding 3'-OH nucleotides to a growing polynucleotide using a complementary polynucleotide, and that may polymerize 3'-blocked nucleotides at a significantly reduced rate relative to 3'-OH nucleotides, and indeed substantially may not polymerize 3'-blocked nucleotides. As such, a polishing polymerase may be considered to "selectively" polymerize 3'-OH nucleotides. A nonlimiting example of a polishing polymerase is a "thermostable" polymerase, which refers to a polymerase that may function well at relatively high temperatures, e.g., at about 30° C. to about 100° C., or at about 40° C. to about 80° C., or at about 50° C. to about 70° C. Examples of thermostable polymerases include the *Pyrococcus* sp. (strain GB-D) DNA polymerase with trade name DEEP VENT® DNA Polymerase (example working temperature 75° C.), *Thermus aquaticus* DNA polymerase I (Taq polymerase) (example working temperature 75° C.), Bst (example working temperature 65° C.), *Sulfolobus* DNA Polymerase IV (example working temperature 55° C.), and Pfu (Phusion) (example working temperature 75° C.), all of which are commercially available from New England Biolabs, Inc. (Ipswich, MA). Other nonlimiting examples of polishing polymerases include *Escherichia coli* DNA polymerase I proteolytic (Klenow fragment) (example working temperature 37° C.) and Bsu (example working temperature 37° C.), which are commercially available from New England Biolabs, Inc.

As used herein, the terms "primer" and "template" are defined as a polynucleotide having a single strand with a free 3'-OH group. A primer or template can also have a modification at the 5' terminus to allow a coupling reaction or to couple the primer to another moiety. The primer or template length can be any number of bases long and can include a variety of non-natural nucleotides. A primer or template can be blocked at the 3' end to inhibit polymerization until the block is removed.

As used herein, "extending," "extension" or any grammatical equivalents thereof can refer to the addition of dNTPs or ddNTPs to a primer, polynucleotide or other nucleic acid molecule by an extension enzyme such as a polymerase, or ligase.

The 3' position of a nucleotide may be coupled to a "blocking group" which is intended to mean a moiety that inhibits an SBS polymerase from coupling a further nucleotide to that nucleotide until that moiety is removed using a suitable reagent, e.g., is replaced with a hydroxyl (OH) group. A nonlimiting example of a blocking group is an azidomethyl group, which may be removed using a tertiary phosphine such as tris-(hydroxypropyl)-phosphine (THPP) or other suitable reducing agent. Another nonlimiting example of a blocking group is an acetal or thiocarbamate 3'-OH blocking group, which may be removed using an organometallic catalyst such as Pd(0)$THPP_n$. A blocking group may be coupled to the 3' position of a nucleotide using any suitable chemistry.

As used herein, the terms "label" and "detectable moiety" are intended to mean a structure that is coupled to a nucleotide and based upon which the presence of the nucleotide can be detected, e.g., using suitable circuitry. A label or detectable moiety may include a moiety to which a fluorophore may be coupled indirectly. For example, the nucleotide may be coupled to include a first moiety, and a detectable moiety (such as a fluorophore) be coupled to a second moiety that becomes coupled to the first moiety, so as to indirectly couple the detectable moiety to the nucleotide.

As used herein, the term "substrate" refers to a material used as a support for compositions described herein. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. In some examples, substrates used in the present application include silica-based substrates, such as glass, fused silica, or other silica-containing material. In some examples, silica-based substrates can include silicon, silicon dioxide, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof. In particular examples, the substrate has at least one surface including glass or a silicon-based polymer. In some examples, the substrates can include a metal. In some such examples, the metal is gold. In some examples, the substrate has at least one surface including a metal oxide. In one example, the surface includes a tantalum oxide or tin oxide. Acrylamides, enones, or acrylates may also be utilized as a substrate material or component. Other substrate materials can include, but are not limited to gallium arsenide, indium phosphide, aluminum, ceramics, polyimide, quartz, resins, polymers and copolymers. In some examples, the substrate and/or the substrate surface can be, or include, quartz. In some other examples, the substrate and/or the substrate surface can be, or include, semiconductor, such as GaAs or ITO. The foregoing lists are intended to be illustrative of, but not limiting to the present application. Substrates can include a single material or a plurality of different materials. Substrates can be composites or laminates. In some examples, the substrate includes an organo-silicate material.

Substrates can be flat, round, spherical, rod-shaped, or any other suitable shape. Substrates may be rigid or flexible. In some examples, a substrate is a bead or a flow cell, or a bead located in a flow cell.

Substrates can be non-patterned, textured, or patterned on one or more surfaces of the substrate. In some examples, the substrate is patterned. Such patterns may include posts, pads, wells, ridges, channels, or other three-dimensional concave or convex structures. Patterns may be regular or irregular across the surface of the substrate. Patterns can be formed, for example, by nanoimprint lithography or by use of metal pads that form features on non-metallic surfaces, for example.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that can be used in methods and compositions set forth herein include, but are not limited to, those commercially available from Illumina, Inc. (San Diego, CA). Beads may be located in a flow cell.

As used herein, "surface" can refer to a part of a substrate or support structure that is accessible to contact with reagents, beads or analytes. The surface can be substantially flat or planar. Alternatively, the surface can be rounded or contoured. Example contours that can be included on a surface are wells, depressions, pillars, ridges, channels or the like. Example materials that can be used as a substrate or support structure include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon, carbon-fibre; metal; inorganic glass; optical fibre bundle, or a variety of other polymers. A single material or mixture of several different materials can form a surface useful in certain examples. In some examples, a surface comprises wells. In some examples, a support structure can include one or more layers. Example support structures can include a chip, a film, a multi-well plate, and a flow cell.

As used herein, "bead" can refer to a small body made of a solid material. The material of the bead may be rigid or semi-rigid. The body can have a shape characterized, for example, as a sphere, oval, microsphere, or other recognized particle shape whether having regular or irregular dimensions. In some examples, a bead or a plurality of beads can comprise a surface. Example materials that are useful for beads include glass such as modified or functionalized glass; plastic such as acrylic, polystyrene or a copolymer of styrene and another material, polypropylene, polyethylene, polybutylene, polyurethane or TEFLON; polysaccharides or cross-linked polysaccharides such as agarose or Sepharose; nylon; nitrocellulose; resin; silica or silica-based materials including silicon and modified silicon; carbon-fiber; metal; inorganic glass; or a variety of other polymers. Example beads include controlled pore glass beads, paramagnetic beads, thoria sol, Sepharose beads, nanocrystals and others known in the art. Beads can be made of biological or non-biological materials. Magnetic beads are particularly useful due to the ease of manipulation of magnetic beads using magnets at various processes of the methods described herein. Beads used in certain examples can have a diameter, width or length from about 5.0 nm to about 100 μm, e.g., from about 10 nm to about 100 μm, e.g., from about 50 nm to about 50 μm, e.g., from about 100 nm to about 500 nm. In some examples, beads used in certain examples can have a diameter, width or length less than about 100 μm, 50 μm, 10 μm, 5 μm, 1 μm, 0.5 μm, 100 nm, 50 nm, 10 nm, 5 nm, 1 nm, 0.5 nm, 100 pm, or any diameter, width or length within a range of any two of the foregoing diameters, widths or lengths. Bead size can be selected to have reduced size, and hence get more features per unit area, whilst maintaining sufficient signal (template copies per feature) in order to analyze the features.

In some examples, polynucleotides, such as capture probes or codes can be coupled to beads. In some examples, the beads can be distributed into wells on the surface of a substrate, such as a flow cell. Example bead arrays that can be used in certain examples include randomly ordered BEADARRAY technology (Illumina Inc., San Diego CA). Such bead arrays are disclosed in Michael et al., Anal Chem 70, 1242-8 (1998); Walt, Science 287, 451-2 (2000); Fan et al., Cold Spring Harb Symp Quant Biol 68:69-78 (2003); Gunderson et al., Nat Genet 37:549-54 (2005); Bibikova el al. Am J Pathol 165:1799-807 (2004); Fan et al., Genome Res 14:878-85 (2004); Kuhn et al., Genome Res 14:2347-56 (2004); Yeakley et al., Nat Biotechnol 20:353-8 (2002); and Bibikova et al., Genome Res 16:383-93 (2006), each of which is incorporated by reference in its entirety.

As used herein, a "polymer" refers to a molecule including a chain of many subunits that are coupled to one another and that may be referred to as monomers. The subunits may repeat, or may differ from one another. Polymers can be biological or synthetic polymers. Example biological polymers that suitably can be included within a label include polynucleotides, polypeptides, polysaccharides, polynucleotide analogs, and polypeptide analogs. Example polynucleotides and polynucleotide analogs include DNA, enantiomeric DNA, RNA, PNA (peptide-nucleic acid), morpholinos, and LNA (locked nucleic acid). Polymers may include spacer phosphoramidites, which may be coupled to polynucleotides but which lack nucleobases, such as commercially available from Glen Research (Sterling, VA). Example synthetic polypeptides can include charged or neutral amino acids as well as hydrophilic and hydrophobic residues. Example synthetic polymers include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(w-alkenoic acid esters), poly(alkyl methacrylates), and other polymeric chemical and biological linkers such as described in Hermanson, Bioconjugate Techniques, third edition, Academic Press, London (2013). Synthetic polymers may be conductive, semiconductive, or insulating.

Figure 1B:
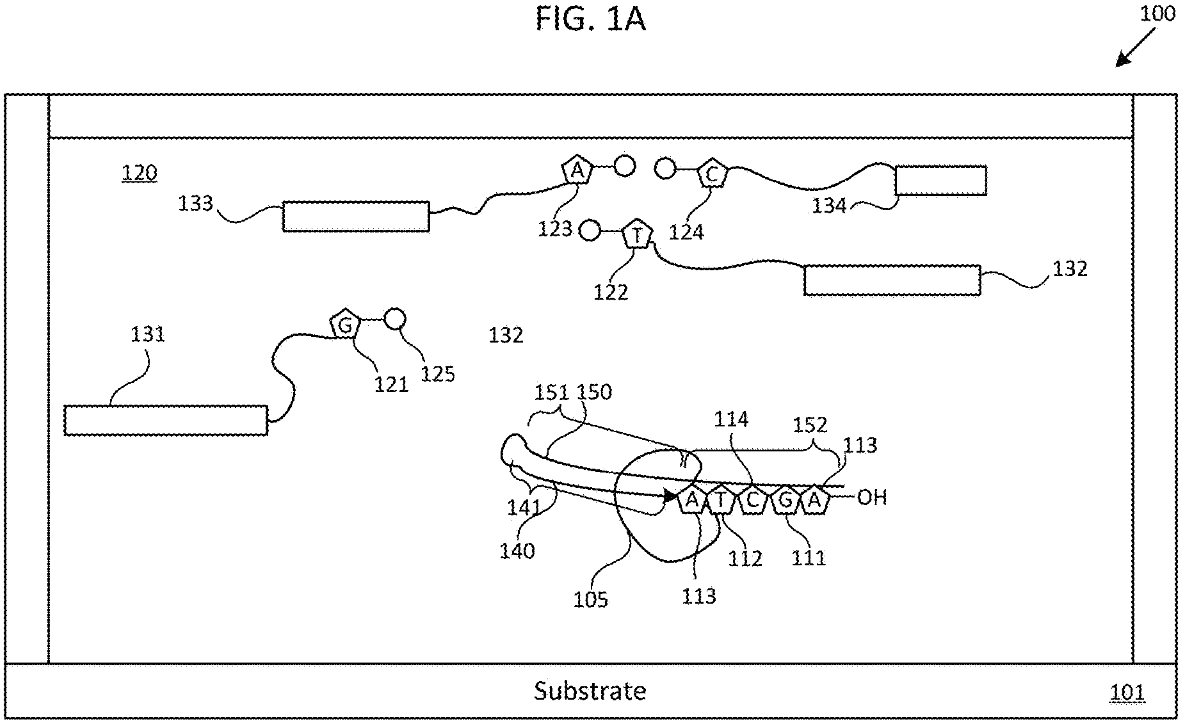

Example Methods for Purifying and Polymerizing 3'-Blocked Nucleotides, and Associated Compositions FIGS. 1A-1B schematically illustrate example compositions and operations in a process flow for purifying 3'-blocked nucleotides. Referring now to FIG. 1A, composition 100 includes substrate 101, such as a flow cell, and solution 120. Solution 120 may include water; 3'-blocked nucleotides 121, 122, 123, 124 each including a blocking group 125 at the 3' position; 3'-OH nucleotides 111, 112, 113, and 114 each including a hydroxyl group instead of a blocking group at the 3' position; polishing polymerase 105; and template 150. In some examples, each of the 3'-blocked nucleotides 121, 122, 123, 124 may include a detectable moiety (which also may be referred to as a label). Illustratively, 3'-blocked nucleotide 121 (G) may include detectable moiety 131, 3'-blocked nucleotide 122 (T) may include detectable moiety 132, 3'-blocked nucleotide 123 (A) may include detectable moiety 133, and 3'-blocked nucleotide 124 (C) may include detectable moiety 134. In some examples, each of the 3'-OH nucleotides 111, 112, 113, 114 may include the same detectable moieties as the corresponding 3'-blocked nucleotides, e.g., because the 3'-OH nucleotides may result from degradation of 3'-blocked nucleotides, or may have remained after a less than 100% conversion of 3'-OH nucleotides to 3'-blocked nucleotides when adding blocking groups 125. As such, 3'-OH nucleotide 111 (G) may include detectable moiety 131, 3'-OH nucleotide 112 (T) may include detectable moiety 132, 3'-OH nucleotide 113 (A) may include detectable moiety 133, and 3'-OH nucleotide 114 (C) may include detectable moiety 134. Suitable linkers 135 (a single such linker being labeled in FIG. 1A) may couple labels to corresponding 3'-OH nucleotides or 3'-blocked nucleotides, and may be provided using any suitable methods known in the art, such as n-hydroxysuccinimide (NHS) ester chemistry or click chemistry.

The 3'-OH nucleotides 111, 112, 113, 114 are selectively polymerizable using polishing polymerase 105 and template 150. Polishing polymerase 105 may have a significantly higher affinity for polymerizing 3'-OH nucleotides 111, 112, 113, 114 as compared to the 3'-blocked nucleotides 121, 122, 123, 124. As such, polishing polymerase 105 may be considered to be specific to the 3'-OH nucleotides. At the particular time illustrated in FIG. 1A, polishing polymerase 105 polymerizes the particular 3'-OH nucleotide that it is binding (illustratively, nucleotide 113), by incorporating into growing polynucleotide 140 using the sequence of template 150 to which polynucleotide 140 is complementary. Additionally, because the remaining 3'-OH nucleotides 111, 112, 113, 114 lack blocking groups 125, polishing polymerase 105 polymerizes such nucleotides as it binds them to extend polynucleotide 140 using the sequence of polynucleotide 150 (illustratively, in the sequence ATCGA), while the 3'-blocked nucleotides remain substantially in solution 120, in a manner such as illustrated in FIG. 1B. As such, polishing polymerase 105 reduces the concentration of 3'-OH nucleotides in solution 120 relative to 3'-blocked nucleotides, and thus may be considered to sequester the 3'-OH nucleotides in such a manner as to reduce, or even substantially eliminate, the availability of the 3'-OH nucleotides to be polymerized together with the 3'-blocked nucleotides, e.g., in a manner such as described with reference to FIGS. 2A-2B.

Polynucleotide 150 may have any suitable sequence that polymerase 105 may use to polymerize 3'-OH nucleotides in solution 120. For example, polynucleotide 150 may include a plurality of abasic nucleotides (N) to which any of 3'-OH nucleotides may hybridize, e.g., five or more abasic nucleotides, ten or more abasic nucleotides, fifteen or more abasic nucleotides, or twenty or more abasic nucleotides. The abasic nucleotides may be adjacent to one another, e.g., forming a sequence NNN . . . N. In some examples, the present compositions and methods may include use of a primer 141 that binds to polynucleotide 150 and that is extended to form polynucleotide 140 using the polymerized 3'-OH nucleotides using the sequence of polynucleotide 150. In some examples, primer 141 may be free-floating in solution 120, e.g., may be added in approximately equimolar amount, or in excess, as polynucleotide 150, and may hybridize to complementary primer 151 of polynucleotide 150.

In other examples such as illustrated in FIGS. 1A-1B, the present compositions and methods may include use of primer 141 that is linked to polynucleotide 150 via loop oligonucleotide 142 and hybridized to complementary primer 151, such that the primer and complementary primer may hybridize to one another to form a hairpin loop, and the primer may not float freely in solution 120. In one nonlimiting example, a hairpin loop may include a sequence with a first portion including a primer 141, a second portion 142 (which may be referred to as a loop oligonucleotide), a third portion 151 that is complementary to the first portion (which may be referred to as a complementary primer) and that is linked to the first portion via the second portion, and a fourth portion 152 including a plurality of abasic nucleotides that may be adjacent to one another. The first portion 141 may hybridize to the third portion 151, and polymerase 105 may add 3'-OH nucleotides to the first portion 141 using the sequence of the fourth portion 152. In one purely illustrative example, primer 141, loop oligonucleotide 142, complementary primer 151, and fourth portion 152 may include the sequence:

```
                                    (SEQ ID NO: 1)
5'-NNNNNNNNNNNNNNNNNNNNcggccatataactggt

agcttTTTTaagctaccagttatatggccg-3'
```

in which primer 141 (first portion) includes the aagctaccagttatatggcc (SEQ ID NO: 2) portion of the sequence, loop oligonucleotide 142 (second portion) includes the TTTT portion of the sequence, complementary primer 151 (third portion) includes the cggccatataactggtagctt (SEQ ID NO: 3) portion of the sequence and folds back onto and hybridizes to the aagctaccagttatatggcc portion of the sequence, and the fourth portion 152 includes the NNNNNNNNNNNNNNNNNNNN (SEQ ID NO: 4) portion of the sequence. It will be appreciated that the first portion 141, second portion 142, and third portion 151 may have any suitable sequences of nucleotides selected such that the first and third portions are complementary to one another and are coupled to one another via the second portion such that the first and third portions may hybridize to one another. It also will be appreciated that the fourth portion 152 may have any suitable sequence of nucleotides selected such that 3'-OH nucleotides may be polymerized using polymerase 105, e.g., so as to extend polynucleotide 140 using primer 141 and the sequence of fourth portion 152.

Although FIG. 1B may suggest that five 3'-OH nucleotides are polymerized using a template 150, it should be appreciated that any suitable number of 3'-OH nucleotides may be polymerized using respective templates in solution 120. For example, about one 3'-OH template may be polymerized using a respective template 150, about two 3'-OH nucleotides may be polymerized using a respective template 150, about three 3'-OH nucleotides may be polymerized using a respective template 150, about four 3'-OH nucleotides may be polymerized using a respective template 150, about five 3'-OH nucleotides may be polymerized using a respective template 150, or more than about five 3'-OH nucleotides may be polymerized using a respective template 150.

The initial concentration in solution 120 of 3'-OH nucleotides may be about 5% or more, and polishing polymerase 105 may reduce the concentration in solution 120 of 3'-OH nucleotides to about 2% or less, or about 1% or less, or about 0.5% or less, or about 0.2% or less, or about 0.1% or less, or about 0.05% or less, or about 0.02% or less, or about 0.01% or less, or even to about 0%. In another example, the initial concentration in solution 120 of 3'-OH nucleotides may be about 2% or more, and polishing polymerase 105 may reduce the concentration in solution 120 of 3'-OH nucleotides to about 1% or less, or about 0.5% or less, or about 0.2% or less, or about 0.1% or less, or about 0.05% or less, or about 0.02% or less, or about 0.01% or less, or even to about 0%. In another example, the initial concentration in solution 120 of 3'-OH nucleotides may be about 1% or more, and polishing polymerase 105 may reduce the concentration in solution 120 of 3'-OH nucleotides to about 0.5% or less, or about 0.2% or less, or about 0.1% or less, or about 0.05% or less, or about 0.02% or less, or about 0.01% or less, or even to about 0%. In another example, the initial concentration in solution 120 of 3'-OH nucleotides may be about 0.5% or more, and polishing polymerase 105 may reduce the concentration in solution 120 of 3'-OH nucleotides to about 0.2% or less, or about 0.1% or less, or about 0.05% or less, or about 0.02% or less, or about 0.01% or less, or even to about 0%. In another example, the initial concentration in solution 120 of 3'-OH nucleotides may be about 0.2% or more, and polishing polymerase 105 may reduce the concentration in solution 120 of 3'-OH nucleotides to about 0.1% or less, or about 0.05% or less, or about 0.02% or less, or about 0.01% or less, or even to about 0%. In another example, the initial concentration in solution 120 of 3'-OH nucleotides may be about 0.1% or more, and polishing polymerase 105 may reduce the concentration in solution 120 of 3'-OH nucleotides to about 0.05% or less, or about 0.02% or less, or about 0.01% or less, or even to about 0%.

Illustratively, polishing polymerase 105 may reduce the concentration of 3'-OH nucleotides in solution 120 by about 10% as compared to the initial concentration of 3'-OH nucleotides in that solution, or may reduce the concentration of 3'-OH nucleotides in solution 120 by about 20% as compared to the initial concentration of 3'-OH nucleotides in that solution, or may reduce the concentration of 3'-OH nucleotides in solution 120 by about 30% as compared to the initial concentration of 3'-OH nucleotides in that solution, or may reduce the concentration of 3'-OH nucleotides in solution 120 by about 40% as compared to the initial concentration of 3'-OH nucleotides in that solution, or may reduce the concentration of 3'-OH nucleotides in solution 120 by about 50% as compared to the initial concentration of 3'-OH nucleotides in that solution, or may reduce the concentration of 3'-OH nucleotides in solution 120 by about 60% as compared to the initial concentration of 3'-OH nucleotides in that solution, or may reduce the concentration of 3'-OH nucleotides in solution 120 by about 70% as compared to the initial concentration of 3'-OH nucleotides in that solution, or may reduce the concentration of 3'-OH nucleotides in solution 120 by about 80% as compared to the initial concentration of 3'-OH nucleotides in that solution, or may reduce the concentration of 3'-OH nucleotides in solution 120 by about 90% as compared to the initial concentration of 3'-OH nucleotides in that solution, or may reduce the concentration of 3'-OH nucleotides in solution 120 by about 95% as compared to the initial concentration of 3'-OH nucleotides in that solution, or may reduce the concentration of 3'-OH nucleotides in solution 120 by about 98% as compared to the initial concentration of 3'-OH nucleotides in that solution, or may reduce the concentration of 3'-OH nucleotides in solution 120 by about 99% as compared to the initial concentration of 3'-OH nucleotides in that solution, or may reduce the concentration of 3'-OH nucleotides in solution 120 by about 99.9% as compared to the initial concentration of 3'-OH nucleotides in that solution, or may reduce the concentration of 3'-OH nucleotides in solution 120 by about 99.99% as compared to the initial concentration of 3'-OH nucleotides in that solution, or may reduce the concentration of 3'-OH nucleotides in solution 120 by about 100% as compared to the initial concentration of 3'-OH nucleotides in that solution.

Solution 120 described with reference to FIGS. 1A-1B may be prepared in any suitable manner. In one example, solution 120 is prepared by adding water, polishing polymerase 105, and template 150 (which may include portions 141, 142, and 151, 152) to a lyophilized mixture of 3'-blocked nucleotides 121, 122, 123, 124 and 3'-OH nucleotides 111, 112, 113, 114. For example, the lyophilized mixture of 3'-blocked nucleotides and 3'-OH nucleotides may be sufficiently stable for storage or shipping, and may be reconstituted with water and mixed with the polishing polymerase and template prior to purifying the 3'-blocked nucleotides. In another example, solution 120 is prepared by adding water to a lyophilized mixture of 3'-blocked nucleotides, 121, 122, 123, 124, 3'-OH nucleotides 111, 112, 113, 114, polishing polymerase 105, and template 150 (which may include portions 141, 142, and 151, 152). For example, the lyophilized mixture of 3'-blocked nucleotides, 3'-OH nucleotides, polishing polymerase, and template may be sufficiently stable for storage or shipping, and may be reconstituted with water prior to purifying the 3'-blocked nucleotides. Such lyophilized mixtures may, for example, be provided as cakes that may be rehydrated. In still another example, solution 120 is prepared by mixing an aqueous mixture of 3'-blocked nucleotides 121, 122, 123, 124 and 3'-OH nucleotides 111, 112, 113, 114 together with polishing polymerase 105 and template 150 prior to purifying the 3'-blocked nucleotides. For example, although an aqueous mixture of 3'-blocked nucleotides and 3'-OH nucleotides may be somewhat less stable than a lyophilized mixture (e.g., the 3'-blocked nucleotides may be more likely to be hydrolyzed to 3'-OH nucleotides when in solution as compared to when lyophilized), using the present methods to purify the 3'-blocked nucleotides may reduce the need to try to suppress hydrolyzation of the 3'-blocked nucleotides. It will be appreciated that any suitable preparation of solution 120 may include appropriate buffer(s), e.g., salts such as magnesium cations or potassium cations (e.g., via magnesium acetate, potassium acetate, magnesium sulfate, potassium chloride, sodium chloride, or the like), for use in polymerase function.

In some examples, solution 120 (and any lyophilized mixture from which solution 120 may be prepared) may further include a sufficient amount of yeast organic pyrophosphatase (YPP) so as to enhance purification of the 3'-blocked nucleotides. For example, polymerizing the 3'-OH nucleotides 111, 112, 113, 114 may generate pyrophosphate (PPi) in a reversible reaction which may be expressed as:

$$\text{DNA(n)} + \text{dNTP} \underset{\text{Pyrophosphorolysis}}{\overset{\text{Polymerization}}{\rightleftharpoons}} \text{DNA(n+1)} + \text{PPi.}$$

In some examples, YPP may be mixed with the other components of solution 120 so as to remove pyrophosphate from the solution as the 3'-OH nucleotides 111, 112, 113, 114 are polymerized, thus driving the reversible reaction forward so as to increase a rate at which additional 3'-OH nucleotides are polymerized (added to the growing strand) as compared to such rate in the absence of YPP.

In some examples, solution 120 (and any lyophilized mixture from which solution 120 may be prepared) may further include a modified α-cyclodextrin, modified β-cyclodextrin, or modified γ-cyclodextrin. A nonlimiting example of a modified α-cyclodextrin is (2-hydroxypropyl)-α-cyclodextrin. Nonlimiting examples of modified β-cyclodextrins include (2-hydroxypropyl)-β-cyclodextrin (HPBCD) and (2-hydroxyethyl)-β-cyclodextrin (HEBCD). A nonlimiting example of a modified γ-cyclodextrin is (2-hydroxypropyl)-γ-cyclodextrin. The modified α-cyclodextrin, modified β-cyclodextrin, or modified γ-cyclodextrin may be used in conjunction with YPP, or may be used without YPP. The modified α-cyclodextrin, modified β-cyclodextrin, or modified γ-cyclodextrin may promote solubility of the nucleotides and/or may inhibit the formation of one or more byproducts in the solution, such as diphosphate or tetraphosphate. For example, solution 120 may include magnesium ions for use by the polishing polymerase and/or by the SBS polymerase (e.g., at a concentration of at least about 1 mM, or about 1 mM to about 6 mM). The nucleotides (3'-blocked and 3'-OH) may be coupled to detectable moieties, such as fluorescent dyes, that may be used to distinguish the nucleotides from one another during an SBS to be performed at a later time. Without wishing to be bound by any theory, it is believed that when the nucleotides in solution 120 have a relatively high concentration (e.g., at least about 0.5 mM), the magnesium ions may reduce solubility of nucleotides and/or of the detectable moieties, e.g., fluorescent dyes, coupled thereto. The modified α-cyclodextrin, modified β-cyclodextrin, or modified γ-cyclodextrin may be included in a sufficient amount to enhance solubility of the nucleotides and/or of the detectable moieties in solution 120, and thus may mitigate any reduction in solubility that otherwise may be caused by the magnesium ions. Illustratively, the modified α-cyclodextrin, modified β-cyclodextrin, or modified γ-cyclodextrin may have a concentration in solution 120 of about 1% to about 10% weight/volume (w/v), e.g., about 2% to about 5% (w/v), or about 5% to about 9% (w/v), or may have a concentration in solution 120 of greater than about 10% (w/v). Other solution conditions suitably may be adjusted so as to enhance solubility of the nucleotides and/or of the fluorescent dyes coupled thereto in solution 120. For example, the concentration of the nucleotides may be sufficiently reduced to maintain solubility, optionally with the use of modified α-cyclodextrin, modified β-cyclodextrin, or modified γ-cyclodextrin, e.g., to a concentration of less than about 1.5 mM, e.g., about 0.1 mM to about 1.5 mM, or about 0.5 to about 1.0 mM.

Figure 2A:
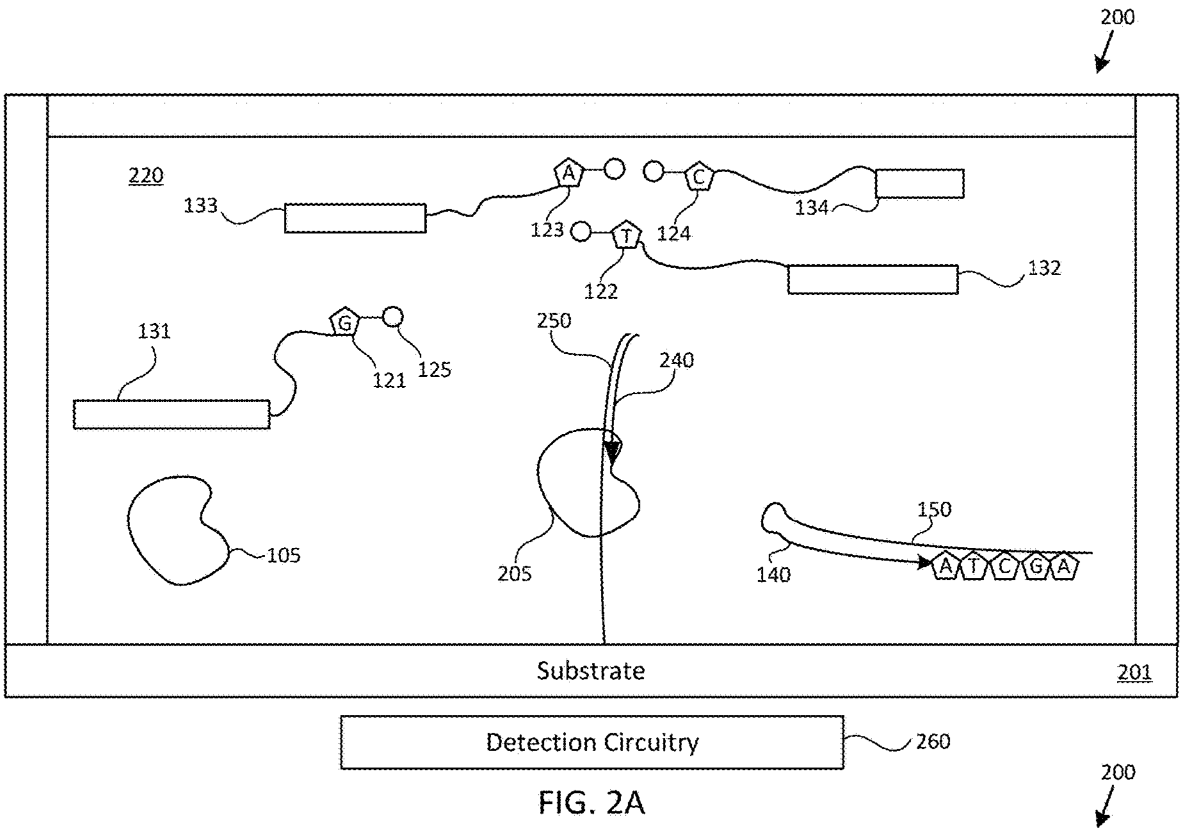
FIGS. 2A-2B schematically illustrate example compositions and operations in a process flow for polymerizing 3'-blocked nucleotides that have been purified to remove 3'-OH nucleotides.
Figure 2B:
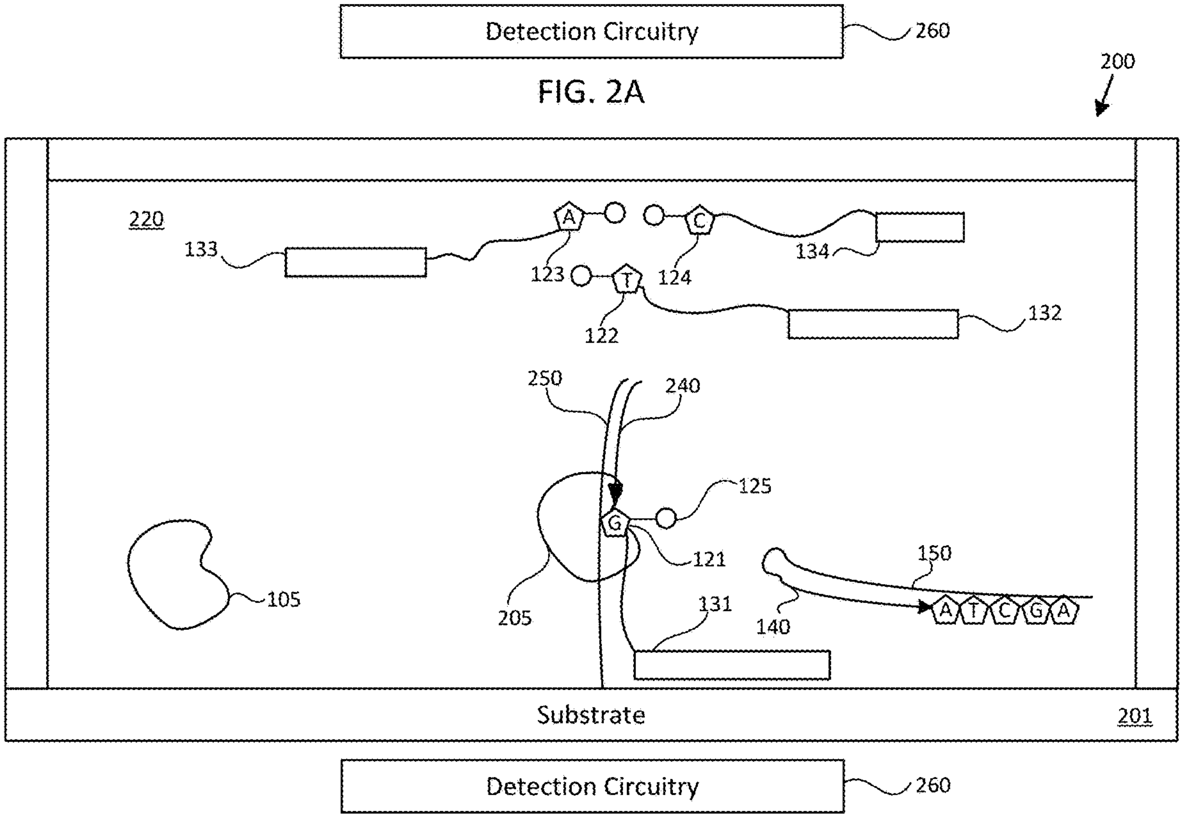

Following purification of 3'-blocked nucleotides, e.g., such as described with reference to FIGS. 1A-1B, the 3'-blocked nucleotides may be polymerized. For example, FIGS. 2A-2B schematically illustrate example compositions and operations in a process flow for polymerizing 3'-blocked nucleotides that have been purified to remove 3'-OH nucleotides. Referring now to FIG. 2A, composition 200 includes substrate 201, such as a flow cell, solution 220, and template 250 that may be coupled to substrate 201. Solution 220 may include water; 3'-blocked nucleotides 121, 122, 123, 124 each including a blocking group 125 at the 3' position; and SBS polymerase 205. In some examples, each of the 3'-blocked nucleotides 121, 122, 123, 124 may include a detectable moiety (which also may be referred to as a label), e.g., detectable moieties 131, 132, 133, 134 which may be coupled to the 3'-blocked nucleotides via suitable linkers 135 in a manner such as described with reference to FIGS. 1A-1B. The 3'-blocked nucleotides 121, 122, 123, 124 are polymerizable using SBS polymerase 205 and template 250. For example, although SBS polymerase 205 may, in principle, be capable of binding any 3'-OH nucleotides 111, 112, 113, 114 or 3'-blocked nucleotides 121, 122, 123, 124 that are in solution 220 at a particular time (e.g., may be nonspecific for 3'-blocked and 3'-OH nucleotides), the concentration of the 3'-OH nucleotides in solution 220 may be reduced or eliminated using purification operations at an earlier time. As such, SBS polymerase 205 may bind and polymerize 3'-blocked nucleotides 121, 122, 123, 124 substantially without binding and polymerizing any 3'-OH nucleotides.

At the particular time illustrated in FIG. 2B, SBS polymerase 205 polymerizes the particular 3'-blocked nucleotide that it is binding (illustratively, nucleotide 121), by incorporating into growing polynucleotide 240 using the sequence of template 250 to which polynucleotide 240 is complementary. Additionally, because 3'-blocked nucleotide 121 includes blocking group 125, SBS polymerase 205 may not polymerize another such nucleotide unless and until blocking group 125 is removed. Detection circuitry 260 may detect and identify detectable moiety 131 while SBS 205 binds nucleotide 121, and thereby may identify nucleotide 121 and its complementary nucleotide within template 250. After blocking group 125 is removed, then SBS polymerase 205 may incorporate an additional 3'-blocked nucleotide which detection circuitry 260 may identify using that nucleotide's detectable moiety. Illustratively, detectable moieties 131, 132, 133, 134 may include one or more fluorophores and detection circuitry 260 may include an optical detection circuit such as a camera, but it will be appreciated that the present methods and compositions are not limited to detecting nucleotides via fluorescence or optical detection of such fluorescence.

Solution 220 described with reference to FIGS. 2A-2B may be prepared in any suitable manner. In one example, solution 220 is prepared by mixing SBS polymerase 205 together with the 3'-blocked nucleotides 121, 122, 123, 124 obtained from purification operations such as described with reference to FIGS. 1A-1B. In the particular example illustrated in FIGS. 2A-2B, solution 220 further may include polymerized 3'-OH hybridized to template 150, e.g., resulting from purification operations such as described with reference to FIGS. 1A-1B. For example, it may be expected that polymerized 3'-OH nucleotides hybridized to template 150 may not significantly affect or impede polymerization of 3'-blocked nucleotides 121, 122, 123, 124, and as such it may not be necessary to remove polymerized 3'-OH nucleotides 140 hybridized to template 150 from solution 220 before polymerizing 3'-blocked nucleotides 121, 122, 123, 124. Solution 220 also, or alternatively, further may include polishing polymerase 105. For example, it may be expected that polishing polymerase 105 may not significantly affect or impede polymerization of 3'-blocked nucleotides 121, 122, 123, 124, and as such it may not be necessary to remove polishing polymerase from solution 220 before polymerizing 3'-blocked nucleotides 121, 122, 123, 124. Accordingly, in one nonlimiting example, solution 220 is prepared by adding SBS polymerase 205 to solution 120 after reducing the concentration, in solution 120, of 3'-OH nucleotides 111, 112, 113, 114 relative to 3'-blocked nucleotides 121, 122, 123, 124, e.g., in a manner such as described with reference to FIGS. 1A-1B, and contacting template 250 with solution 220. In some examples, the concentration in solution 120 of 3'-OH nucleotides 111, 112, 113, 114 relative to 3'-blocked nucleotides 121, 122, 123, 124 is reduced in the presence of template 250, and solution 220 is prepared by adding SBS polymerase 205, in the presence of template 250, to solution 120 after such reduction. In other examples, the concentration in solution 120 of 3'-OH nucleotides 111, 112, 113, 114 (FIG. 1B) relative to 3'-blocked nucleotides 121, 122, 123, 124 is reduced elsewhere, solution 220 is prepared by adding SBS polymerase 205 to solution 120 after such reduction, and then solution 220 is brought into contact with template 250. If additives such as YPP or a modified α-cyclodextrin, modified β-cyclodextrin, or modified γ-cyclodextrin are included in solution 120, then such additives also may be present in solution 220.

Figure 3:
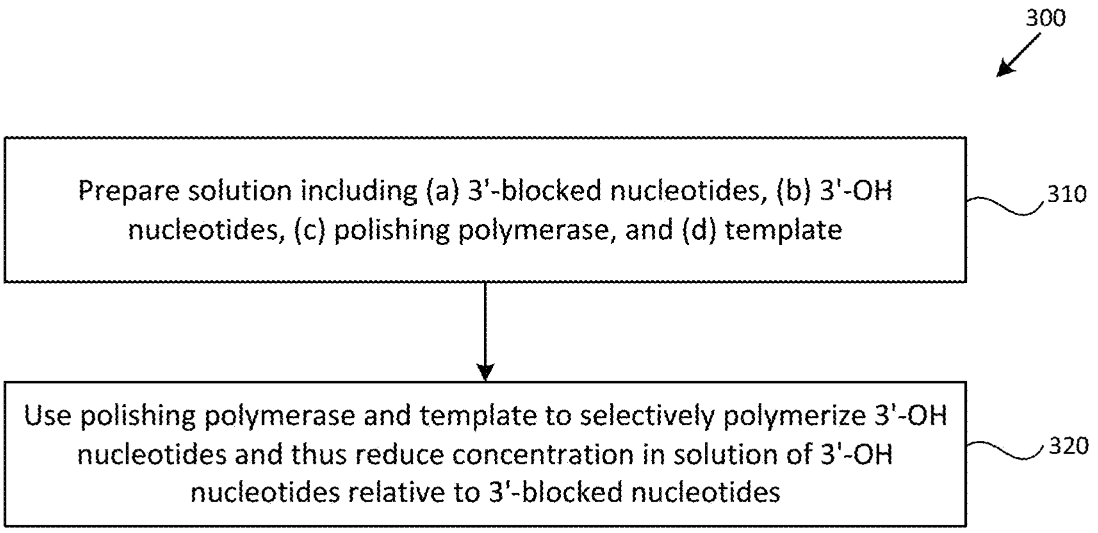
FIG. 3 illustrates an example flow of operations in a method for purifying 3'-blocked nucleotides.

It will be appreciated that the present compositions may be used in any suitable method for purifying or polymerizing 3'-blocked nucleotides. Illustratively, FIG. 3 illustrates an example flow of operations in a method for purifying 3'-blocked nucleotides. Method 300 illustrated in FIG. 3 may include preparing a solution comprising (a) 3'-blocked nucleotides, (b) 3'-OH nucleotides, (c) a polishing polymerase, and (d) a template (operation 310). For example, solution 120 described with reference to FIGS. 1A-1B may be prepared that includes (a) 3'-blocked nucleotides 121, 122, 123, 124; (b) 3'-OH nucleotides 111, 112, 113, 114; (c) polishing polymerase 105; and (d) template 150. In some examples, preparing the solution may include adding water, the polishing polymerase, and the template to a lyophilized mixture of the 3'-blocked nucleotides and the 3'-OH nucleotides. In other examples, preparing the solution may include adding water to a lyophilized mixture of the 3'-blocked nucleotides, the 3'-OH nucleotides, the polishing polymerase, and the template. In some examples, each of the 3'-blocked nucleotides includes a detectable moiety, e.g., detectable moieties 131, 132, 133, 134 described with reference to FIGS. 1A-1B.

Method 300 illustrated in FIG. 3 further may include using the polishing polymerase and the template to selectively polymerize the 3'-OH nucleotides and thus reduce a concentration in the solution of the 3'-OH nucleotides relative to the 3'-blocked nucleotides (operation 320). For example, polishing polymerase 105 and template 150 may be used to selectively polymerize 3'-OH nucleotides 111, 112, 113, 114 and thus reduce a concentration of those nucleotides in solution 120 relative to 3'-blocked nucleotides 121, 122, 123, 124 in a manner such as described with reference to FIGS. 1A-1B. The solution may be heated while using the polishing polymerase and the template during operation 320. For example, different polishing polymerases may have different temperatures at which they may efficiently and selectively polymerize 3'-OH nucleotides. Illustratively, the solution may be heated to a temperature of about 30-75° C., e.g., to a temperature of about 40-60° C. However, it should be appreciated that the particular temperature(s) for performing operation 320 may be selected based at least on the particular polishing polymerase being used, and its performance to polymerize the particular 3'-OH nucleotides in solution. In some examples, the solution may be heated using a cache manifold that includes an inner sleeve, an outer sleeve, and a spiral tube through which the solution flows, wherein at least one of the inner sleeve and the outer sleeve is heated. Nonlimiting examples of such a cache manifold are described with reference to FIGS. 5A-5B and 6A-6D.

Figure 4:
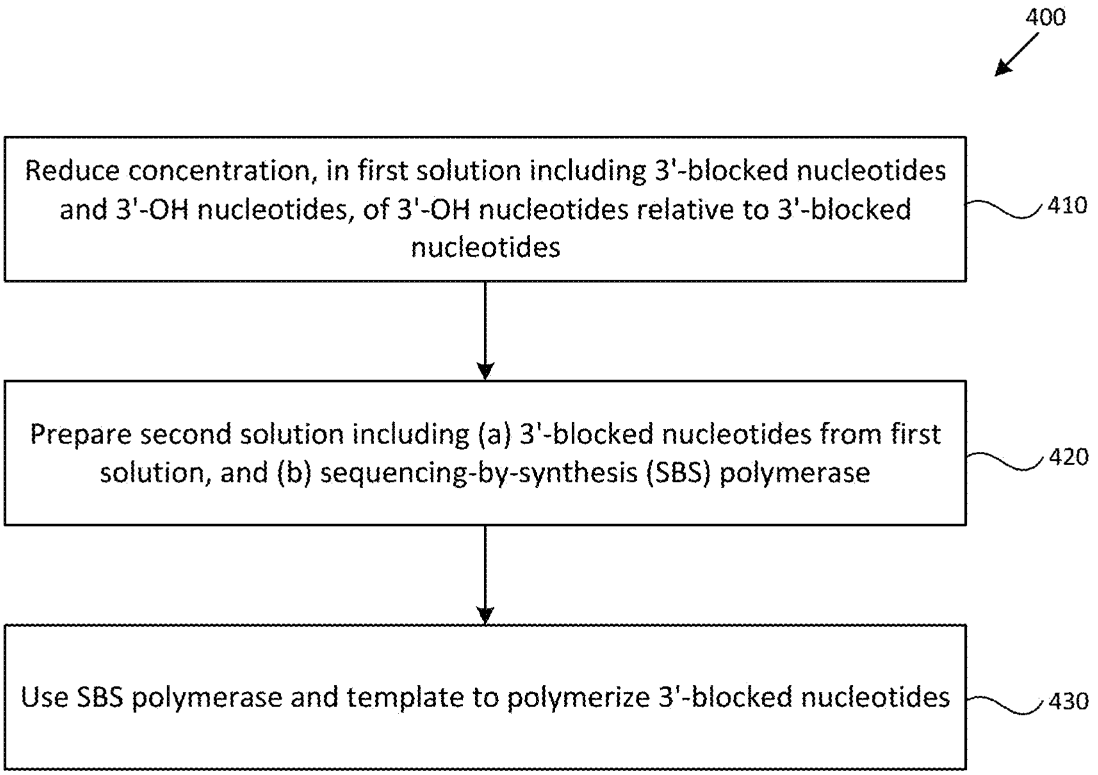
FIG. 4 illustrates an example flow of operations in a method for polymerizing 3'-blocked nucleotides that have been purified to remove 3'-OH nucleotides.

FIG. 4 illustrates an example flow of operations in a method for polymerizing 3'-blocked nucleotides that have been purified to remove 3'-OH nucleotides. Method 400 illustrated in FIG. 4 may include reducing a concentration, in a first solution including 3'-blocked nucleotides and 3'-OH nucleotides, of the 3'-OH nucleotides relative to the 3'-blocked nucleotides (operation 410). Operations 310 and 320 described with reference to FIG. 3 provide a non-limiting example of the manner in which operation 410 may be performed. For example, operation 410 may include reducing the concentration, in solution 120, of 3'-OH nucleotides 111, 112, 113, 114 relative to 3'-blocked nucleotides 121, 122, 123, 124 by selectively polymerizing the 3'-OH nucleotides using polishing polymerase 105 and template 150, e.g., in a manner such as described with reference to FIGS. 1A-1B and 3.

Method 400 illustrated in FIG. 4 may include preparing a second solution comprising (a) the 3'-blocked nucleotides from the first solution, and (b) an SBS polymerase (operation 420). For example, solution 220 described with reference to FIGS. 2A-2B may be prepared that includes (a) 3'-blocked nucleotides 121, 122, 123, 124 from solution 120 (FIGS. 1A-1B), and (b) SBS polymerase 205. In a manner such as described with reference to FIGS. 1A-1B, solution 120 further may include polishing polymerase 105, and additionally or alternatively further may include the polymerized 3'-OH nucleotides. Illustratively, preparing the second solution may include adding SBS polymerase 205 to solution 120 after reducing the concentration, in the solution 120, of 3'-OH nucleotides 111, 112, 113, 114 relative to 3'-blocked nucleotides 121, 122, 123, 124. Operation 420 may be, but need not necessarily, performed in the presence of template 250.

Method 400 illustrated in FIG. 4 may include using the SBS polymerase and the first template to polymerize the 3'-blocked nucleotides (operation 430). For example, SBS polymerase 205 may use template 250 to polymerize 3'-blocked nucleotides 121, 122, 123, 124 in a manner such as described with reference to FIGS. 2A-2B. Because fewer (and in some examples, substantially no) 3'-OH nucleotides 111, 112, 113, 114 (FIGS. 1A-1B) may be in in solution 220 (FIGS. 2A-2B), the sequence of template 250 (FIGS. 2A-2B) may be determined more accurately than if solution 220 instead were to include a greater number or concentration of 3'-OH nucleotides 111, 112, 113, 114. For example, each of the 3'-blocked nucleotides in solutions 120 and 220 may include a detectable moiety. Method 400 may include detecting the detectable moieties of the 3'-blocked nucleotides while the 3'-blocked nucleotides are being polymerized using the SBS polymerase and the first template, e.g., in a manner such as described with reference to FIGS. 2A-2B.

It should be appreciated that operations 320 and 430 may be performed using any suitable components. In one nonlimiting example, polishing polymerase 105 and template 150 are used in a sequencing-by-synthesis instrument during operation 320. SBS polymerase 205 and template 250 may, in some examples, be used on the same instrument as the 3'-blocked nucleotides are purified using a separate operation. That is, the polishing polymerase and the SBS polymerase both may be used on the same sequencing-by-synthesis instrument, though at different times. As such, the 3'-blocked nucleotides may be purified at any suitable time prior to polymerizing them, and even may be purified immediately before polymerizing them, thus reducing or inhibiting conversion of the 3'-blocked nucleotides to 3'-OH nucleotides before polymerization.

Figure 5A:
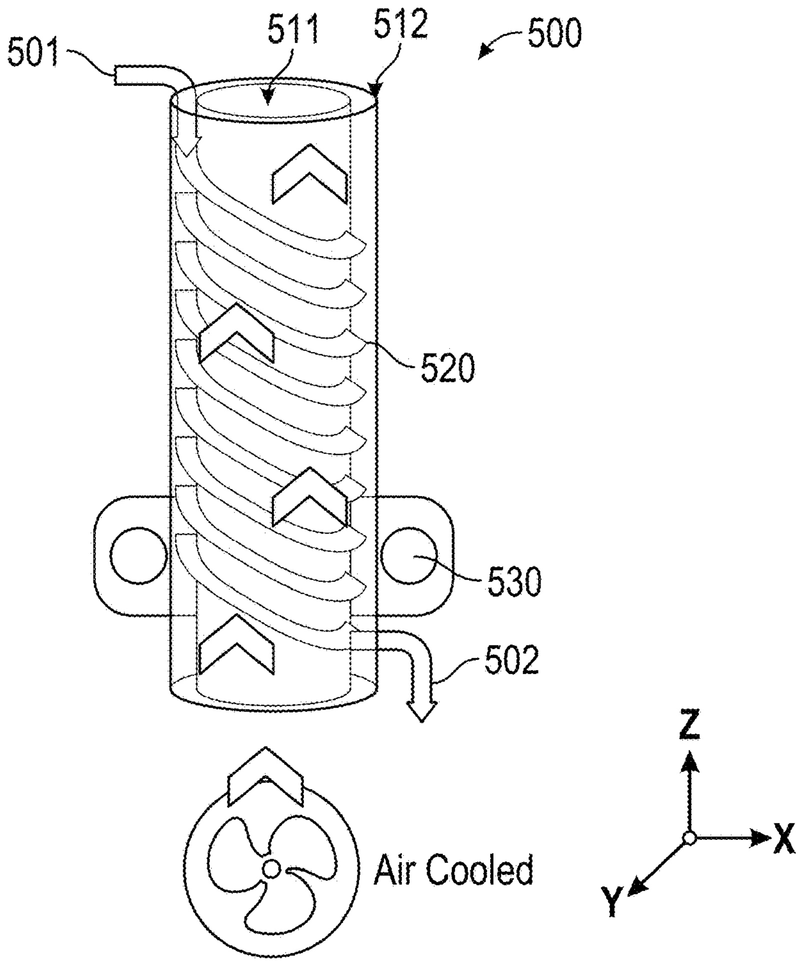
FIGS. 5A-5B schematically illustrate an example temperature control device.
Figure 5B:
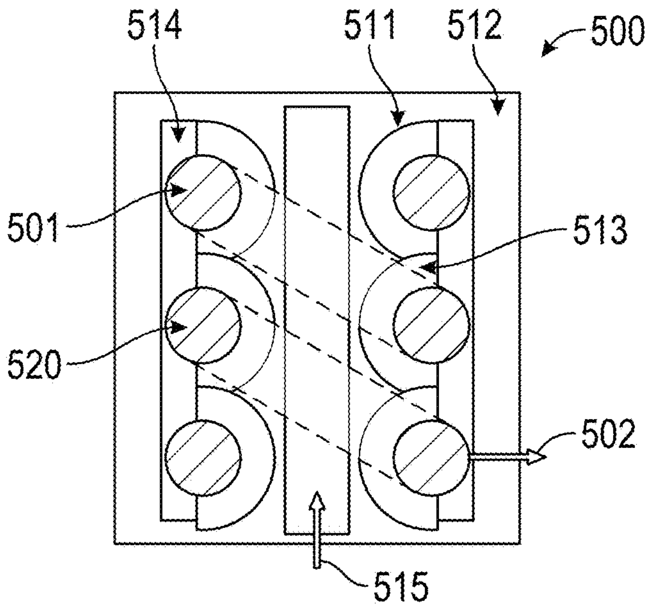

As noted further above, different polymerases may function differently at different temperatures. For example, the particular polishing polymerase used in operation 320 of method 300 may function appropriately at a higher or lower temperature than the particular SBS polymerase used in operation 430 of method 400. FIGS. 5A-5B schematically illustrate an example temperature control device 500, e.g., that may be used to heat or cool solution 120 described with reference to FIGS. 1A-1B or solution 220 described with reference to FIGS. 2A-2B. Device 500, illustrated in perspective view in FIG. 5A and in cross-sectional view in FIG. 5B, may be referred to herein as a "cache manifold." Device 500 includes inlet 501, outlet 502, inner structure 511, outer sleeve 512, spiral tube 520, and mounting structure 530. Inlet 501 may be coupled to spiral tube 520 which passes between inner structure 511 and outer sleeve 512. Inner structure 511 may be heated or cooled, and outer sleeve 512 may be heated or cooled. In the nonlimiting example illustrated in FIGS. 5A-5B, inner structure 511 may be cooled, e.g., using air cooling, or may be heated, e.g., using heating element 515 (such as a flowing, heated fluid or a resistive heating element) disposed within inner structure 511. For example, inner structure 511 may include an inner sleeve providing a lumen through which fluid may flow so as provide heating or cooling, or may contact heating element, such as a resistive heating element 515.

During use, inlet 501 may receive a fluid (e.g., solution 120 or 220) to be heated or cooled. The fluid passes through spiral tube 520 and is heated or cooled via thermal contact with one or both of inner structure 511 and outer sleeve 512 before exiting device 500 at outlet 502. For example, inner structure 511 may include a scalloped core 513 into which spiral tube 520 fits along the length of device 500, thus thermally contacting spiral tube 520 with inner structure 511. Spiral tube 520 may be thermally joined to outer sleeve 512 using thermal potting material 514. Device 500 may be provided in a sequencing-by-synthesis instrument, or any other suitable system or apparatus, for use in controlling temperature of a fluid. For example, mounting structure 530 may include apertures via which device 500 may be secured into place e.g., within a sequencing-by-synthesis instrument, such as within the fluid flow path between reagent reservoirs and the substrate at which purification or polymerization (or both purification and polymerization) of 3'-blocked nucleotides is performed. Device 500 may be used to heat or cool a solution to any suitable temperature, e.g., a temperature suitable for using a polishing polymerase in a manner such as described with reference to FIGS. 1A-1B and 3, or a temperature suitable for using an SBS polymerase in a manner such as described with reference to FIGS. 2A-2B and 4.

It will be appreciated that device 500 may have any suitable dimensions. For example, device 500 may have a length of about 10 mm to about 1 m, or about 50 mm to about 500 mm, or about 50 mm to about 200 mm. Additionally, or alternatively, inner structure 511 may have an inner diameter of about 5 mm to about 80 mm, or about 10 mm to about 50 mm. Additionally, or alternatively, outer sleeve 512 may have an outer diameter of about 10 mm to about 100 mm, or about 20 mm to about 50 mm. In one nonlimiting example, device 500 has a length of about 100 mm, inner structure 511 may have an inner diameter of about 50 mm, and outer sleeve 512 may have an outer diameter of about 70 mm. Illustratively, spiral tube 620 may have a volume of about 4 ml.

Figure 6A:
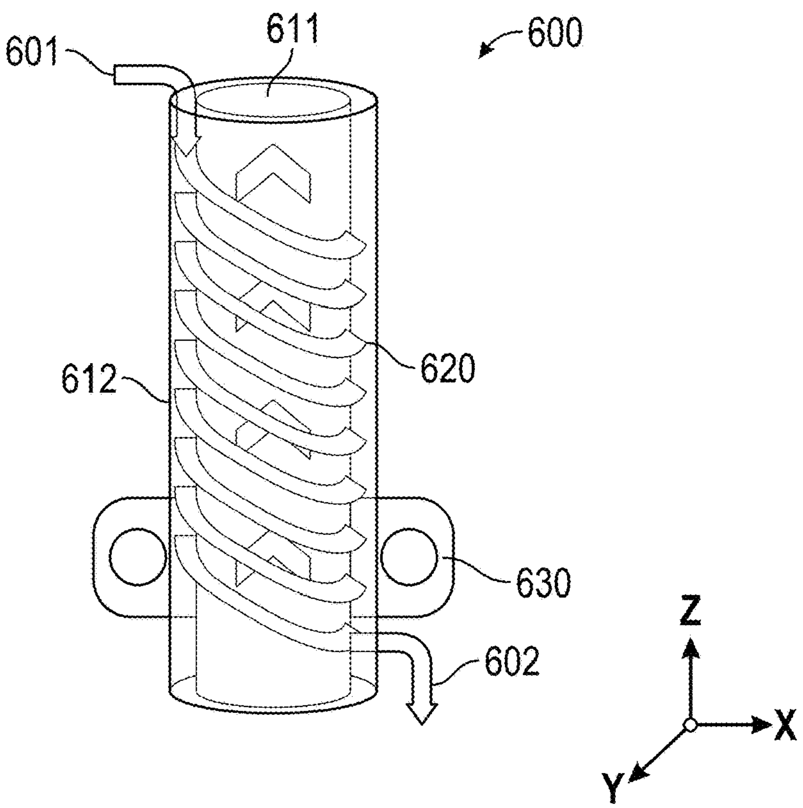
FIGS. 6A-6D schematically illustrate another example temperature control device.
Figure 6B:
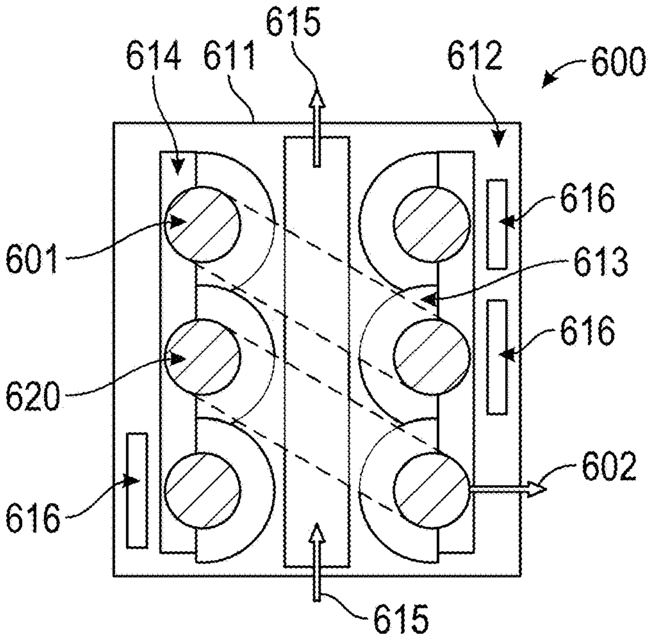
Figure 6C:
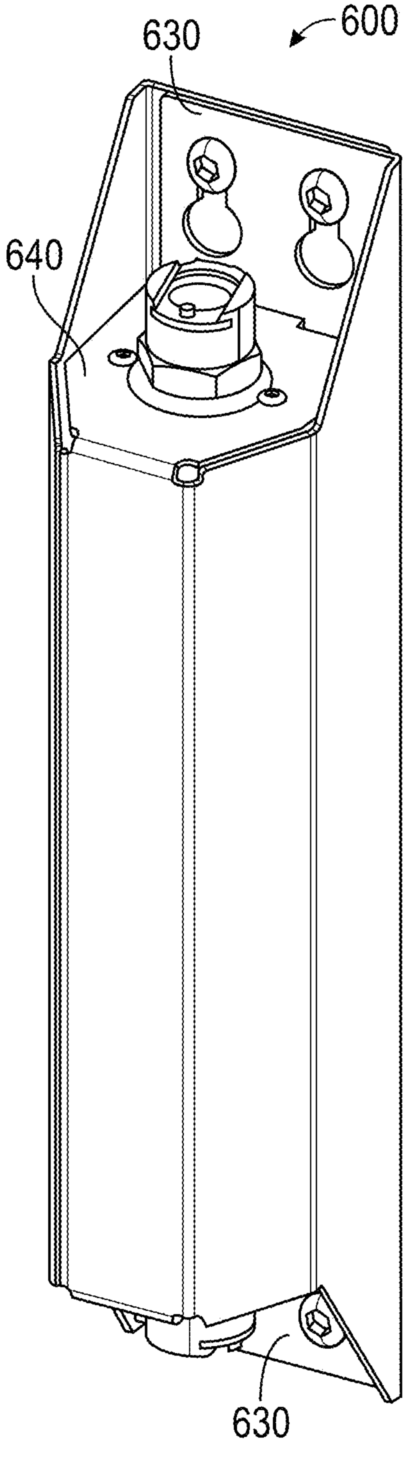
Figure 6D:
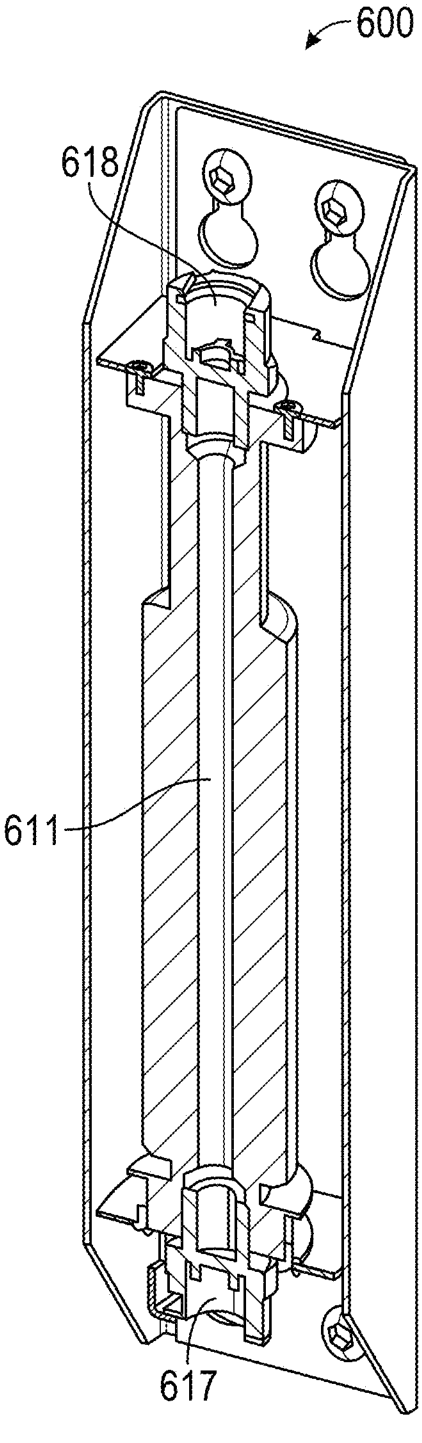

FIGS. 6A-6D schematically illustrate another example temperature control device, e.g., solution 120 described with reference to FIGS. 1A-1B or solution 220 described with reference to FIGS. 2A-2B. Temperature control device 600, illustrated in perspective view in FIG. 6A and in cross-sectional view in FIG. 6B, may be referred to herein as a "cache manifold." Device 600 includes inlet 601, outlet 602, inner sleeve 611, outer sleeve 612, spiral tube 620, and mounting structure 630. Inlet 601 may be coupled to spiral tube 620 which passes between inner sleeve 611 and outer sleeve 612. Inner sleeve 611 may be heated or cooled, and outer sleeve 612 may be heated or cooled. In the nonlimiting example illustrated in FIGS. 6A-6B, inner sleeve 611 may be cooled or may be heated, e.g., using heating/cooling element 615 (such as a flowing, heated or cooled fluid) disposed within inner sleeve 611. Outer sleeve 612 may be cooled or may be heated, e.g., using heating element 616 (such as a resistive heating element) disposed within outer sleeve 612. During use, inlet 601 may receive a fluid (e.g., solution 120 or 220) to be heated or cooled. The fluid passes through spiral tube 620 and is heated or cooled via thermal contact with one or both of inner sleeve 611 and outer sleeve 612 before exiting device 600 at outlet 602. For example, inner sleeve 611 may include a scalloped core 613 into which spiral tube 620 fits along the length of device 600, thus thermally contacting spiral tube 620 with inner sleeve 611. Spiral tube 620 may be thermally joined to outer sleeve 612 using thermal potting material 614. Device 600 may be provided in a sequencing-by-synthesis instrument, or any other suitable system or apparatus, for use in controlling temperature of a fluid, such as within the fluid flow path between reagent reservoirs and the substrate at which purification or polymerization (or both purification and polymerization) of 3'-blocked nucleotides is performed. For example, mounting structure 630 may include apertures via which device 600 may be secured into place, e.g., within a sequencing-by-synthesis instrument. FIG. 6C schematically illustrates a perspective view of an example mounting structure 630 and outer housing 640 of device 600. FIG. 6D schematically illustrates a cross-sectional view through outer housing 640 of device 600, in which inlet 617 of inner sleeve 611 and outlet 618 of inner sleeve 611 may be seen. Device 600 may be used to heat or cool a solution to any suitable temperature, e.g., a temperature suitable for using a polishing polymerase in a manner such as described with reference to FIGS. 1A-1B and 3, or a temperature suitable for using an SBS polymerase in a manner such as described with reference to FIGS. 2A-2B and 4.

It will be appreciated that device 600 may have any suitable dimensions. For example, device 600 may have a length of about 10 mm to about 1 m, or about 50 mm to about 500 mm, or about 50 mm to about 200 mm. Additionally, or alternatively, inner sleeve 611 may have an inner diameter of about 5 mm to about 80 mm, or about 10 mm to about 50 mm. Additionally, or alternatively, outer sleeve 612 may have an outer diameter of about 10 mm to about 100 mm, or about 20 mm to about 50 mm. In one nonlimiting example, device 600 has a length of about 250 mm, inner sleeve 611 may have an inner diameter of about 50 mm, and outer sleeve 612 may have an outer diameter of about 70 mm. Illustratively, spiral tube 620 may have a volume of about 4 ml.

Figure 7A:
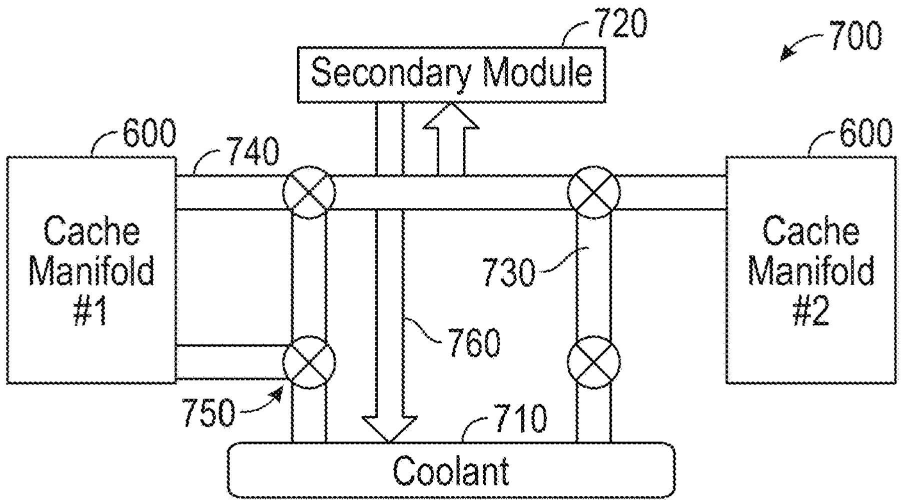
FIGS. 7A-7C schematically illustrate example temperature control systems utilizing one or more temperature control devices.
Figure 7B:
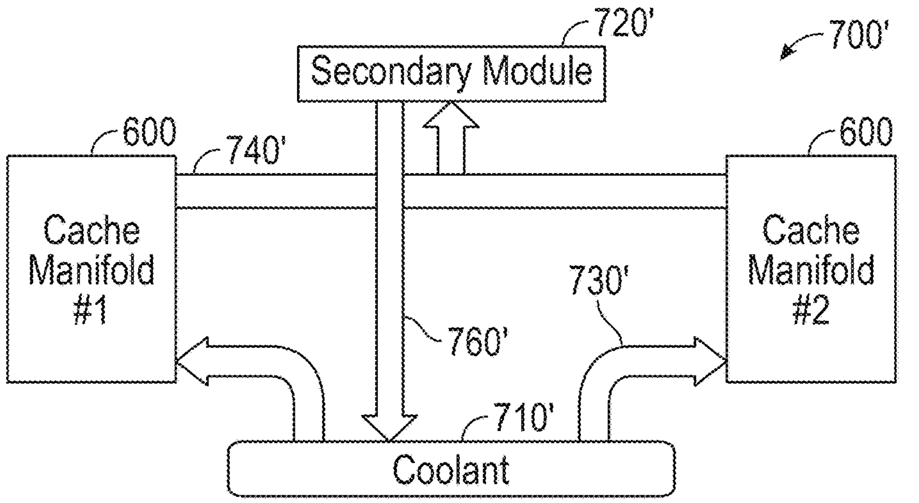
Figure 7C:
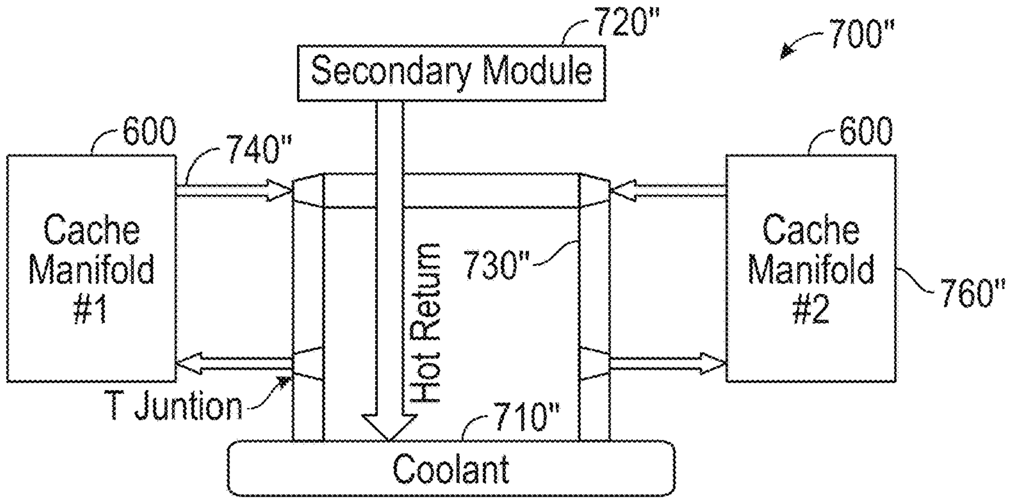

Any suitable number of cache manifolds may be used to heat or cool any suitable number of fluids, e.g., in a sequencing-by-synthesis instrument. Illustratively, FIGS. 7A-7C schematically illustrate example temperature control systems utilizing one or more heating and cooling devices 600 of FIGS. 6A-6D. In the example temperature control system 700 shown in FIG. 7A, coolant reservoir 710 may be coupled to any suitable number of temperature control devices 600, e.g., first and second temperature control devices, and also may be coupled to any other suitable element to be cooled, referred to in FIG. 7A as secondary module 720. For example, coolant reservoir 710 may be coupled to secondary module 720 and to temperature control device(s) 600 via primary coolant lines 730 and secondary coolant lines 740. Illustratively, active valves 750 may be controlled by a suitable control module (not specifically illustrated) so as to actively open or close connections between primary coolant lines 730 and secondary coolant lines 740 via which coolant may be flowed through inner sleeve(s) 611 of temperature control device(s) 600 (FIG. 6A) and then back into primary coolant lines 730. Coolant also may be flowed through primary coolant lines 730 through secondary module 720, and warmed coolant (e.g., as heated by any suitable ones of the cooling device(s) and secondary module 720) returned to coolant reservoir via return line 760. During use, fluid (e.g., solution 120 or solution 220) may be flowed through temperature control device(s) 600 and controllably heated, e.g., using heating element 616 of outer sleeve 612, or cooled, e.g., using coolant flowing through inner sleeve 611 (FIG. 6B). In one nonlimiting example, secondary module 720 includes an illumination module, and coolant reservoir 710 is for cooling both the illumination module and the temperature control device(s) 600.

In the example temperature control system 700' shown in FIG. 7B, coolant reservoir 710' may be coupled to any suitable number of temperature control devices 600, e.g., first and second temperature control devices, and also may be coupled to any other suitable element to be cooled, referred to in FIG. 7B as secondary module 720'. For example, coolant reservoir 710' may be coupled to temperature control device(s) 600 (FIG. 6A) via primary coolant lines 730' via which coolant may be flowed through inner sleeve(s) 611 of temperature control device(s) 600 and then into secondary coolant lines 740'. Coolant then may be flowed to secondary coolant lines 740' and through secondary module 720', and warmed coolant (e.g., as heated by the cooling device(s) and secondary module 720') returned to coolant reservoir via return line 760'. During use, fluid (e.g., solution 120 or solution 220) may be flowed through temperature control device(s) 600 and controllably heated, e.g., using heating element 616 of outer sleeve 612, or cooled, e.g., using coolant flowing through inner sleeve 611 (FIG. 6B). In one nonlimiting example, secondary module 720' includes an illumination module, and coolant reservoir 710' is for cooling both the illumination module and the temperature control device(s) 600.

In the example temperature control system 700" shown in FIG. 7C, coolant reservoir 710' may be coupled to any suitable number of temperature control devices 600, e.g., first and second temperature control devices, and also may be coupled to any other suitable element to be cooled, referred to in FIG. 7C as secondary module 720". For example, coolant reservoir 710" may be coupled to temperature control device(s) 600 (FIG. 6A) via primary coolant lines 730" via which coolant may be flowed through inner sleeve(s) 611 of temperature control device(s) 600 and then into secondary coolant lines 740". Coolant then may be flowed to secondary coolant lines 740" and through secondary module 720", and warmed coolant (e.g., as heated by the cooling device(s) and secondary module 720") returned to coolant reservoir via return line 760". During use, fluid (e.g., solution 120 or solution 220) may be flowed through temperature control device(s) 600 and controllably heated, e.g., using heating element 616 of outer sleeve 612, or cooled, e.g., using coolant flowing through inner sleeve 611 (FIG. 6B). In one nonlimiting example, secondary module 720" includes an illumination module, and coolant reservoir 710"

is for cooling both the illumination module and the temperature control device(s) 600.

WORKING EXAMPLES

Additional examples are disclosed in further detail in the following examples, which are not in any way intended to limit the scope of the claims.

Example 1. Purification Conditions

Figure 8:
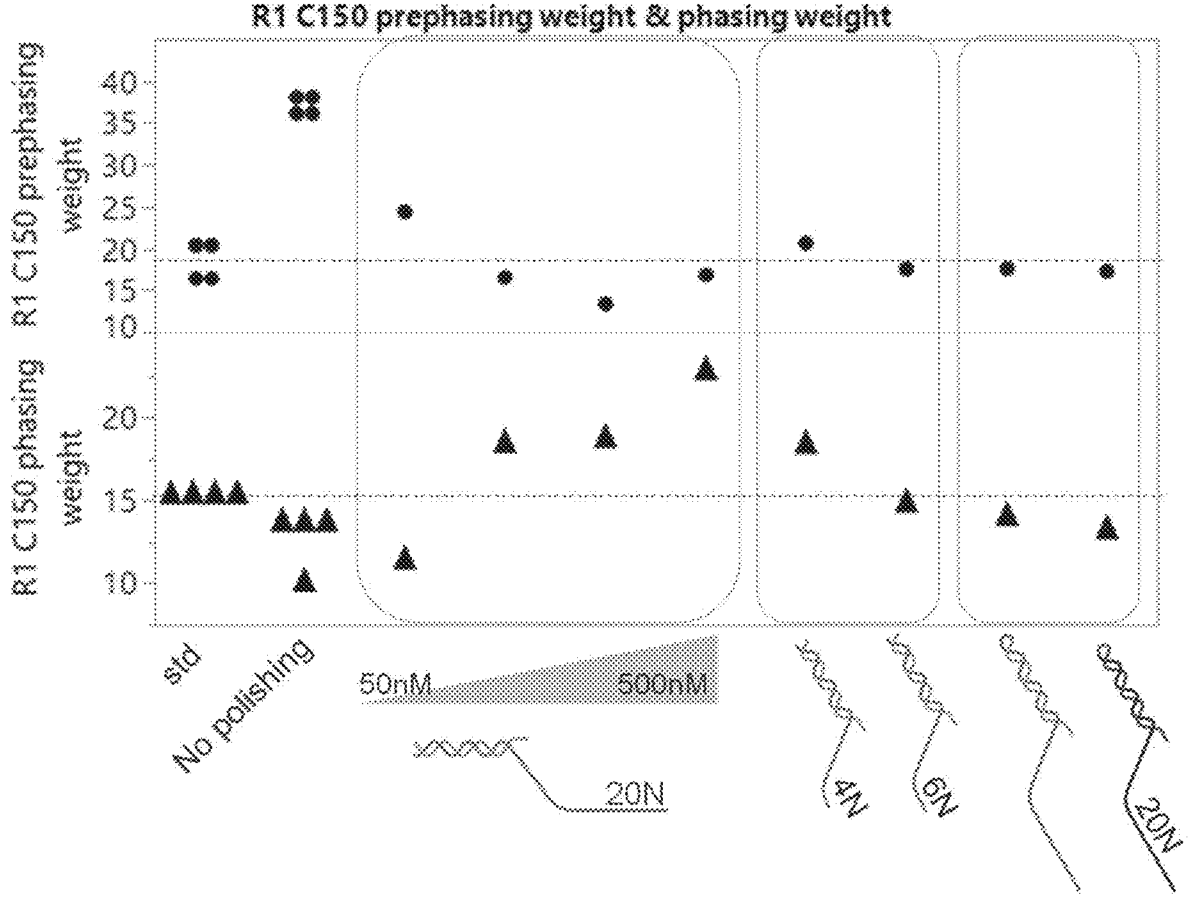
FIG. 8 is a plot of phasing and prephasing during polymerization of 3'-blocked nucleotides that were purified to remove 3'-OH nucleotides using different conditions.

FIG. 8 is a plot of phasing and prephasing during polymerization of 3'-blocked nucleotides that were purified using different conditions. More specifically, an aqueous solution of 3'-blocked nucleotides blocked with azidomethyl groups was heated for 5 hours at 55° C. so as to simulate nucleotide stress conditions and convert a portion of the 3'-blocked nucleotides to 3'-OH nucleotides. The resulting aqueous mixture of 3'-blocked nucleotides and 3'-OH nucleotides was purified for 30 minutes at 37° C. in a manner such as described with reference to FIGS. 1A-1B and 3, using the Klenow polymerase and different conditions, e.g., different templates, and different concentrations of templates, such as described further below. The purified 3'-blocked nucleotides then were used in a sequencing reaction, using 2×151 cycle runs on the MINISEQ® sequencing-by-synthesis instrument (Ilumina, Inc., San Diego CA) using the PhiX library as templates. The purified nucleotides behaved similarly in the two sequencing reads (R1 and R2). The accumulated prephasing over 150 cycles of read 1 (R1 C150% prephasing weight) and the accumulated phasing over 150 cycles of read 1 (R1 C150% phasing weight) after 3'-blocked nucleotide polymerization was measured for the purified 3'-blocked nucleotides, as well as for heated and unpurified 3'-blocked nucleotides and for unheated 3'-blocked nucleotides.

The leftmost data points ("std") in FIG. 8 correspond to polymerization of 3'-blocked nucleotides that had not been heated and therefore contained a baseline lower concentration of 3'-OH nucleotides; these 3'-blocked nucleotides were found to have an R1 C150% phasing weight of about 17% and an R1 C150% prephasing weight of about 16%. The next data points to the right ("No polishing") correspond to polymerization of 3'-blocked nucleotides that had been heated as indicated above, but were not purified, and therefore contained a baseline upper concentration of 3'-OH nucleotides; these 3'-blocked nucleotides were found to have an R1 C150% phasing weight of about 14% and an R1 C150% prephasing weight of about 36%. From a comparison of the "std" data points to the "No polishing" data points, it may be understood that heating 3'-blocked nucleotides significantly increased phasing and prephasing during polymerization.

The effect of concentration of a first example template was determined. More specifically, the next data points to the right ("50 nM") correspond to polymerization of 3'-blocked nucleotides that had been heated as indicated above and were purified using 50 nM of a 20N template of sequence 5'-NNN NNN NNN NNN NNN NNN NNC GGC CAT ATA ACT GGT AGC TT-3' (SEQ ID NO: 5), whereN are degenerated bases, combined in equimolar amount with a primer oligonucleotide sequence AAG CTA CCA GTT ATA TGG CCG (SEQ ID NO: 6). These 3'-blocked nucleotides were found to have an R1 C150 phasing weight of about 12% and an R1 C150 prephasing weight of about 24%. The next data points to the right correspond to polymerization of 3'-blocked nucleotides that had been heated as indicated above and were purified using 200 nM of the same 20N template; these 3'-blocked nucleotides were found to have an R1 C150 phasing weight of about 18.5% and an R1 C150 prephasing weight of about 16.5%. The next data points to the right correspond to polymerization of 3'-blocked nucleotides that had been heated as indicated above and were purified using 300 nM of the same 20N template; these 3'-blocked nucleotides were found to have an R1 C150 phasing weight of about 19% and an R1 C150 prephasing weight of about 13%. The next data points to the right ("500 nM") correspond to polymerization of 3'-blocked nucleotides that had been heated as indicated above and were purified using 500 nM of the same 20N template; these 3'-blocked nucleotides were found to have an R1 C150 phasing weight of about 23% and an R1 C150 prephasing weight of about 17%. From a comparison of the data points corresponding to different concentrations of the 20N template, it may be understood that with increased concentration of 20N template, prephasing approached a similar prephasing as for the unheated ("std") 3'-blocked nucleotides. However, with increased concentration of 20N template, phasing increased significantly.

Different templates were used to determine their effect on phasing and prephasing. More specifically, the next data points to the right ("4N") correspond to polymerization of 3'-blocked nucleotides that had been heated as indicated above and were purified using 200 nM of a 4N template of sequence 5'-NNN NCGGC CAT ATA ACT GGT AGCTT-3' (SEQ ID NO: 7) where N are degenerated bases, combined in equimolar amount with primer oligonucleotide sequence AAG CTA CCA GTT ATA TGG CCG (SEQ ID NO: 6). These 3'-blocked nucleotides were found to have an R1 C150 phasing weight of about 18.5% and an R1 C150 prephasing weight of about 21%. The next data points to the right ("6N") correspond to polymerization of 3'-blocked nucleotides that had been heated as indicated above and were purified using 200 nM of a 6N template of sequence 5'-NNNNNNCGGCCATATAACTGGTAGCTT-3' (SEQ ID NO: 8), combined in equimolar amount with primer oligonucleotide sequence AAG CTA CCA GTT ATA TGG CCG (SEQ ID NO: 6). These 3'-blocked nucleotides were found to have an R1 C150 phasing weight of about 15% and an R1 C150 prephasing weight of about 17.5%. From a comparison of the data points corresponding to different linear template weights, it may be understood that the template with the higher number of N had a prephasing and phasing that was closer to that of the unheated ("std") 3'-blocked nucleotides.

The next data points to the right correspond to polymerization of 3'-blocked nucleotides that had been heated as indicated above and were purified using 200 nM of a mixture of 4 hairpin templates, each template corresponding to one base, of respective sequences GGG GGG GGG GGG CGG CCA TAT AAC TGG TCA CTC CAG TTA TAT GGC CG (hairpin G) (SEQ ID NO: 9), TTT TTT TTT TTT CGG CCA TAT AACTGG TCA CTC CAG TTA TAT GGC CG (hairpin T) (SEQ ID NO: 10), CCC CCC CCC CCC CGG CCA TAT AACTGG TCA CTC CAG TTA TAT GGC CG (hairpin C) (SEQ ID NO: 11), AAA AAA AAA AAA CGG CCA TAT AAC TGG TCA CTC CAG TTA TAT GGC CG (hairpin A) (SEQ ID NO: 12). The hairpin templates were added to the reaction at the same concentration to reach a final concentration of 200 nM of DNA. These 3'-blocked nucleotides were found to have an R1 C150% phasing weight of about 14% and an R1 C150% prephasing weight of about 16%. The next data points to the right correspond to polymerization of 3'-blocked nucleotides that had been heated as indicated above and were purified using 200 nM of a hairpin template containing 20 degenerated bases (N) at the 5' end, having sequence NNN NNN NNN NNN NNN NNN NN CGG CCA TAT AAC TGG TAG CTT TTT TAA GCT ACC AGTT AT ATG GCC G (SEQ ID NO: 1). These 3'-blocked nucleotides were found to have an R1 C150% phasing weight of about 12% and an R1 C150% prephasing weight of about 16%. From a comparison of these two sets of data, it may be understood that both hairpin templates had a prephasing and phasing that were similar, and that were relatively close to that of the unheated ("std") 3'-blocked nucleotides. It also may be understood that the hairpin templates had similar phasing and prephasing as the 6N template.

Example 2. Polymerase and Temperature During Purification

Figure 9:
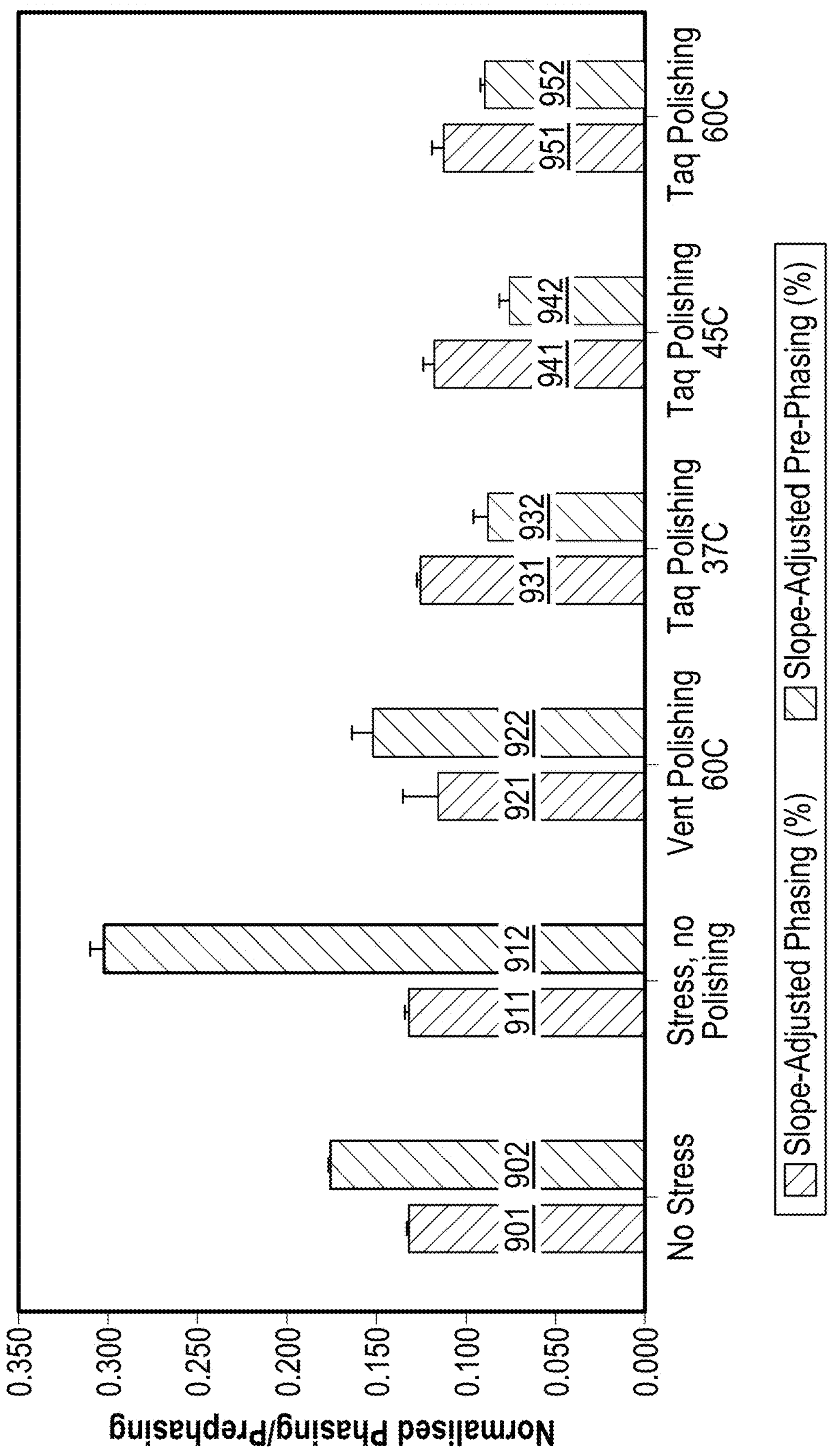
FIG. 9 is a plot of phasing and prephasing during polymerization of 3'-blocked nucleotides that were purified to remove 3'-OH nucleotides using different polymerases and different temperatures.

FIG. 9 is a plot of phasing and prephasing during polymerization of 3'-blocked nucleotides that were purified to remove 3'-OH nucleotides using different polymerases and different temperatures. More specifically, similarly as for Example 1, an aqueous solution of 3'-blocked nucleotides blocked with azidomethyl groups was heated for 5 hours at 55° C. so as to convert a portion of the 3'-blocked nucleotides to 3'-OH nucleotides. The resulting aqueous mixture of 3'-blocked nucleotides and 3'-OH nucleotides was purified for 30 minutes in a manner such as described with reference to FIGS. 1A-1B and 3, using an hp oligomer template with 20 degenerated bases (meaning that at each position, one of the four bases could be incorporated; since this is random, each oligomer should have a different sequence) and different polymerases and different temperatures such as described further below. The purified 3'-blocked nucleotides then were polymerized using 2×26 cycle runs on the MINISEQ® sequencing-by-synthesis instrument (Illumina, Inc., San Diego CA) using the PhiX library as templates. The slope adjusted prephasing and phasing were measured for the purified 3'-blocked nucleotides, as well as for heated and unpurified 3'-blocked nucleotides and for unheated 3'-blocked nucleotides.

The leftmost data points ("no stress") in FIG. 9 is the control, where 3'-blocked nucleotides have not been heated and therefore contained a baseline lower concentration of 3'-OH nucleotides; these 3'-blocked nucleotides were found to have a normalized phasing 901 of about 0.13% and a normalized prephasing 902 of about 0.18%. The next data points to the right ("stress, no polishing") correspond to polymerization of 3'-blocked nucleotides that had been heated for 5 hours at 55 C, but were not purified, and therefore contained a baseline upper concentration of 3'-OH nucleotides; these 3'-blocked nucleotides were found to have a normalized phasing 911 of about 0.14% and a normalized prephasing 912 of about 0.31% From a comparison of the "no stress" data points to the "stress, no polishing" data points, it may be understood that heating 3'-blocked nucleotides significantly increased prephasing during polymerization, and that phasing was not significantly affected.

Different polymerases were used at different temperatures to determine their effect on phasing and prephasing. More specifically, the next data points to the right ("Vent polishing 60 C") correspond to polymerization of 3'-blocked nucleotides that had been heated as indicated above and were purified using the Deep Vent polymerase at 60° C. (DEEP VENT® DNA Polymerase (New England Biolabs, Inc., Ipswich, MA)); these 3'-blocked nucleotides were found to have a normalized phasing 921 of about 0.12% and a normalized prephasing 922 of about 0.15%. The next data points to the right ("Taq polishing 37 C") correspond to polymerization of 3'-blocked nucleotides that had been heated as indicated above and were purified using a Taq polymerase at 37° C.; these 3'-blocked nucleotides were found to have a normalized phasing 931 of about 0.13% and a normalized prephasing 932 of about 0.09%. The next data points to the right ("Taq polishing 45 C") correspond to polymerization of 3'-blocked nucleotides that had been heated as indicated above and were purified using the Taq polymerase at 45° C.; these 3'-blocked nucleotides were found to have a normalized phasing 941 of about 0.12% and a normalized prephasing 942 of about 0.08%. The next data points to the right ("Taq polishing 60 C") correspond to polymerization of 3'-blocked nucleotides that had been heated as indicated above and were purified using the Taq polymerase at 60° C.; these 3'-blocked nucleotides were found to have a normalized phasing 951 of about 0.12% and a normalized prephasing 952 of about 0.09%. From a comparison of performance of the different polymerases, it may be understood that using the Deep Vent polymerase at 60° C. provided similar phasing and prephasing as for the lower baseline "no stress" in which the 3'-blocked nucleotides were not heated. Additionally, it may be understood that using the Taq polymerase at the experimental temperatures provided even less prephasing than for the lower baseline "no stress" in which the 3'-blocked nucleotides were not heated. Accordingly, it may be understood that the Taq polymerase removed from solution not only the 3'-OH nucleotides that were generated using heating, but also at least some of the 3'-OH nucleotides that were present even without heating. Under the particular experimental conditions in this example, the Taq polymerase appeared to provide better performance than Deep Vent, and neither Deep Vent or Taq appeared to detrimentally influence phasing.

Example 3. Mitigating Pyrophosphate Accumulation

Figure 10:
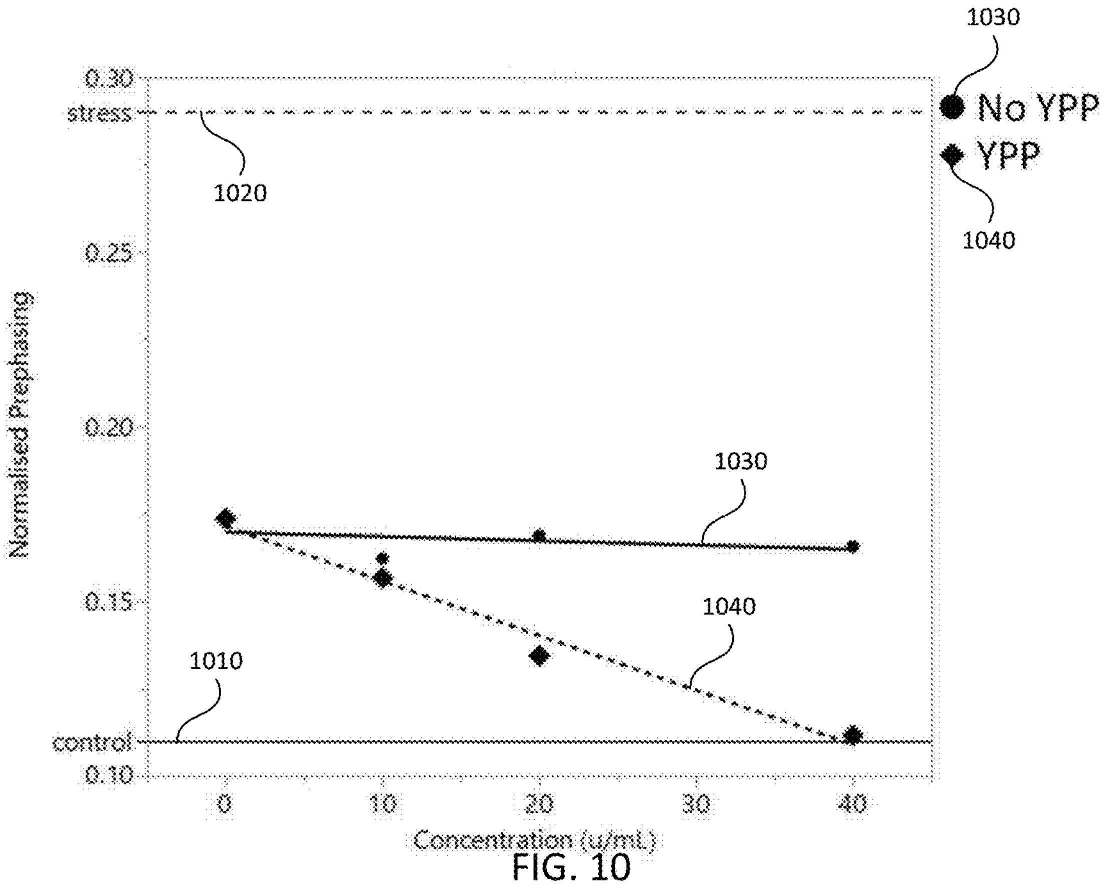
FIG. 10 is a plot of prephasing during polymerization of 3'-blocked nucleotides that were purified to remove 3'-OH nucleotides using Taq polymerase and different concentrations of yeast inorganic pyrophosphatase (YPP).

FIG. 10 is a plot of prephasing during polymerization of 3'-blocked nucleotides that were purified to remove 3'-OH nucleotides using Taq polymerase and yeast inorganic pyrophosphatase (YPP) enzyme. More specifically, the use of YPP enzyme to mitigate accumulation of pyrophosphate during purification, and thus drive forward the polymerization of 3'-OH nucleotides, was measured. Similarly as for Example 1, an aqueous solution of 3'-blocked nucleotides blocked with azidomethyl groups was heated for 5 hours at 55° C. so as to convert a portion of the 3'-blocked nucleotides to 3'-OH nucleotides. The resulting aqueous mixture of 3'-blocked nucleotides and 3'-OH nucleotides was purified for 30 minutes at 37° C. in a manner such as described with reference to FIGS. 1A-1B and 3, using 10× of an hp oligomer template with 20 degenerated bases (NNN NNN NNN NNN NNN NNN NN CGG CCA TAT AAC TGG TAG CTT TTT TAA GCT ACC AGTT AT ATG GCC G (SEQ ID NO: 1)), 10× of Taq polymerase, and varying concentrations of YPP. The purified 3'-blocked nucleotides then were polymerized using 2×26 cycle runs on the MISEQ® sequencing-by-synthesis instrument (Illumina, Inc., San Diego CA) using the PhiX library as templates. The normalized prephasing was measured for the purified 3'-blocked nucleotides, as well as for heated and unpurified 3'-blocked nucleotides and for unheated 3'-blocked nucleotides.

Trace 1010 ("Control") corresponds to polymerization of 3'-blocked nucleotides that had not been heated and therefore contained a baseline lower concentration of 3'-OH nucleotides; these 3'-blocked nucleotides were found to have a normalized prephasing of about 0.11%. Trace 1020 ("Stress") corresponds to polymerization of 3'-blocked nucleotides that had been heated as indicated above, but were not purified, and therefore contained a baseline upper concentration of 3'-OH nucleotides with a normalized prephasing of about 0.29%. From a comparison of traces 1010 and 1020, it may be understood that heating 3'-blocked nucleotides significantly increased normalized prephasing during polymerization. Trace 1030 ("No YPP") corresponds to normalized prephasing for polymerization such as described above without using YPP, while trace 1040 ("YPP") corresponds to normalized prephasing for polymerization using different concentrations of YPP, namely 10 μL, 20 μL, and 40 μL of YIPP. It may be understood from FIG. 10 that the normalized prephasing decreased with increasing concentration of YPP, with the normalized prephasing at 40 μL of YIPP being similar to that of the control. Accordingly, mixing a suitable concentration of YPP into solution 120 may facilitate polymerization of 3'-OH nucleotides and thus purification of 3'-blocked nucleotides.

Figure 11:
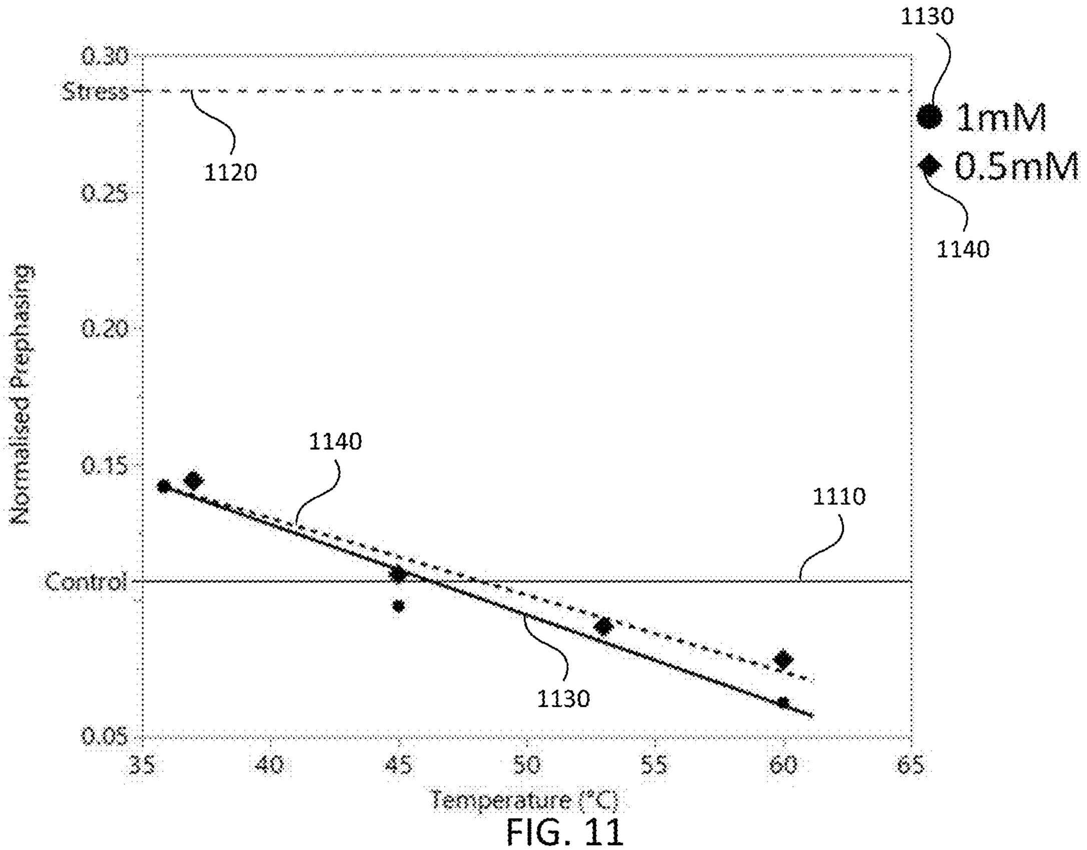
FIG. 11 is a plot of prephasing during polymerization of 3'-blocked nucleotides that were purified to remove 3'-OH nucleotides using different temperatures and concentrations of 3'-OH nucleotides.

Example 4. Effect of Purification Temperature and Concentration of 3'-Blocked Nucleotides FIG. 11 is a plot of prephasing during polymerization of 3'-blocked nucleotides that were purified to remove 3'-OH nucleotides using different temperatures and concentrations of 3'-blocked nucleotides. Similarly as for Example 1, an aqueous solution of 3'-blocked nucleotides blocked with azidomethyl groups was heated for 5 hours at 55° C. so as to convert a portion of the 3'-blocked nucleotides to 3'-OH nucleotides. The resulting aqueous mixture of 3'-blocked nucleotides and 3'-OH nucleotides was purified for 30 minutes in a manner such as described with reference to FIGS. 1A-1B and 3, using 10× of an hp oligomer template with 20 degenerated bases (NNN NNN NNN NNN NNN NNN NN CGG CCA TAT AAC TGG TAG CTT TTT TAA GCT ACC AGTT AT ATG GCC G (SEQ ID NO. 1)), 10× of the Taq polymerase and either 0.5 mM or 1 mM of the heated 3'-blocked nucleotides, at a variety of temperatures. The purified 3'-blocked nucleotides then were polymerized using 2×26 cycle runs on the MISEQ® sequencing-by-synthesis instrument (Illumina, Inc., San Diego CA) using the PhiX library as templates. The normalized prephasing was measured for the purified 3'-blocked nucleotides, as well as for heated and unpurified 3'-blocked nucleotides and for unheated 3'-blocked nucleotides.

Trace 1110 ("Control") corresponds to polymerization of 3'-blocked nucleotides that had not been heated and therefore contained a baseline lower concentration of 3'-OH nucleotides; these 3'-blocked nucleotides were found to have a normalized prephasing of about 0.1%. Trace 1120 ("Stressed Sample") corresponds to polymerization of 3'-blocked nucleotides that had been heated as indicated above, but were not purified, and therefore contained a baseline upper concentration of 3'-OH nucleotides and a normalized prephasing of about 0.29%. From a comparison of traces 1110 and 1120, it may be understood that heating 3'-blocked nucleotides significantly increased normalized prephasing during polymerization. Trace 1130 ("0.5") corresponds to normalized prephasing for polymerization such as described above using a concentration during purification of 0.5 mM of 3'-blocked nucleotides at different temperatures, while trace 1140 ("1") corresponds to normalized prephasing for polymerization such as described above using a concentration during purification of 1 mM of 3'-blocked nucleotides at different temperatures. It may be understood from FIG. 11 that the normalized prephasing decreased with increasing temperature, with the normalized prephasing at 50° C. being similar to that of the control, and the normalized prephasing at 53° C. and at 60° C. being significantly lower than the control. Accordingly, higher temperatures, at least for certain thermostable polymerases such as Taq, may facilitate purification of 3'-blocked nucleotides.

Example 5. Mitigating Reduced Solubility of 3'-Blocked Nucleotides and/or Reducing Byproducts A precipitate was formed and a color change of solution was observed when nucleotides (3'-blocked and 3'-OH), which were coupled to different fluorescent dyes, were mixed with polishing polymerase, a template, magnesium ions (from magnesium acetate), and a buffer. The change in color was interpreted as the solution having a reduced concentration of fluorescent dyes, and the precipitate was interpreted as being an aggregation of the nucleotides coupled to the fluorescent dyes. It was found that similar solutions to which the modified β-cyclodextrin HPBCD also was added did not form a precipitate or change color. From this it was inferred that modified α-cyclodextrins (such as (2-hydroxypropyl)-α-cyclodextrin), other modified β-cyclodextrins (such as (2-hydroxyethyl)-β-cyclodextrin, HEBCD), or modified γ-cyclodextrins (such as (2-hydroxypropyl)-γ-cyclodextrin) may promote solubility of the nucleotides and/or of the fluorescent dyes. A series of solutions were prepared in which the concentration of magnesium ions was varied between 0 and 6.3 mM, the concentration of HPBCD was varied between 0% and 10% (w/v), and the concentration of nucleotides including fluorescent dyes was varied between 0.5 and 1.5 mM. The normalized intensity of the fluorescent dyes in the solution was used as a metric of the stability of the nucleotides in solution, that is, whether the nucleotides (and their fluorescent dyes) stayed in solution or precipitated. The plots described below with reference to FIGS. 12-15 were obtained by using the measured normalized intensities, together with the corresponding concentrations of different solution components, in a model that interpolated the behavior of the solution system for additional concentrations. It may be reasonably expected that modified α-cyclodextrins (such as (2-hydroxypropyl)-α-cyclodextrin), other modified β-cyclodextrins (such as HEBCD), or modified γ-cyclodextrins (such as (2-hydroxypropyl)-γ-cyclodextrin) will exhibit similar behavior in solution as described in the present examples for HPBCD, and that the concentration of the modified α-, β-, or γ-cyclodextrins suitably may be selected without undue experimentation, based on the teachings herein, to achieve similar effect as demonstrated for HPBCD. For example, it may be reasonably expected that the α-derivatives (6-mer structures) and γ-derivatives (8-mer structures) of cyclodextrin will function in a similar way to HPBCD (7-mer structure), and that HEBCD (another 7-mer structure) will function in a similar way to HPBCD.

Figure 12:
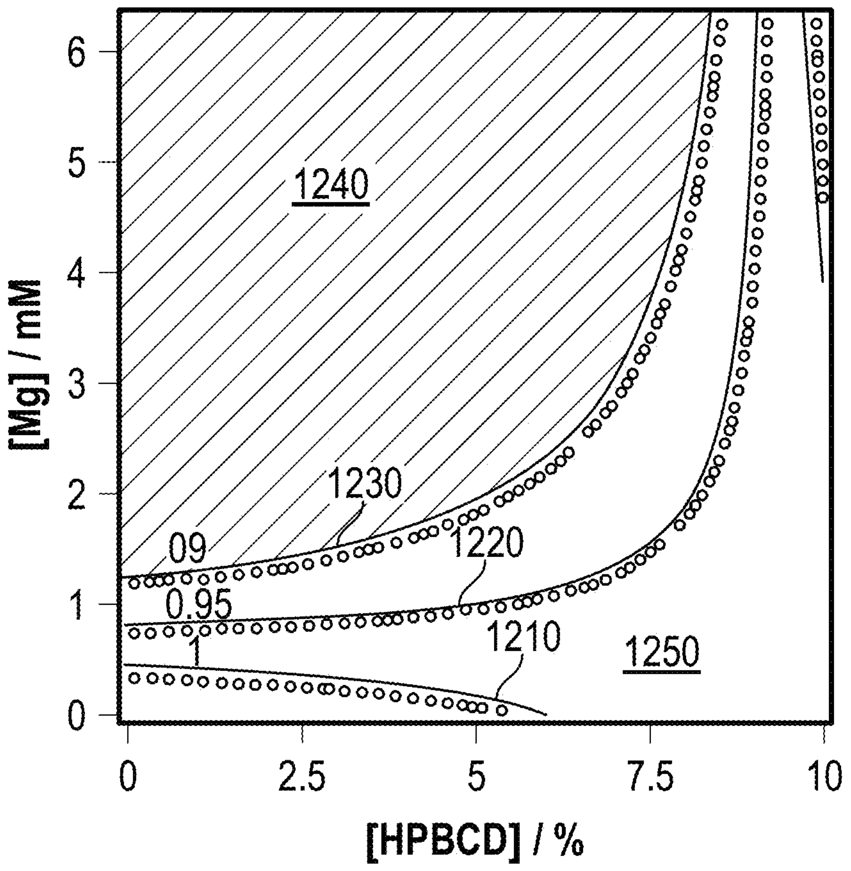
FIG. 12 is a contour plot of the stability of fluorescently labeled nucleotides as a function of concentrations of the modified β-cyclodextrin HPBCD and of magnesium ions.

FIG. 12 is a contour plot of the stability of fluorescently labeled nucleotides as a function of concentrations of the modified β-cyclodextrin HPBCD and of magnesium ions. The nucleotides used in FIG. 12 were named FFC-1, meaning cytidine (C) coupled to a dye referred to as "1". In FIG.

12, the curves 1210, 1220, 1230 respectively correspond to ranges of concentrations of HPBCD and of magnesium ions that, together, provide a stability of FFC-1 of 1.0, 0.95, or 0.90. In this example, a stability of about 0.9 to 1.0 may be considered to be stable, while a stability of less than about 0.90 may be considered to be "unstable" because an insufficient concentration of nucleotides remains in solution to satisfactorily perform SBS. Nucleotide concentration was not significant for this model and therefore the contour plot shown in FIG. 12 covers the 0.5-1.5 mM range of total nucleotide concentration. The solutions used to prepare FIG. 12 included buffer components in the polishing solution, but did not include polymerase or an oligonucleotide template. Shaded region 1240 in FIG. 12 corresponds to combinations of magnesium and HPBCD concentrations for which FFC-1 is unstable. Shaded region 1240 in FIG. 12 corresponds to combinations of magnesium and HPBCD concentrations for which FFC-1 is unstable. It may be seen that curve 1210 (stability 1.0) corresponds to concentrations of magnesium varying from about 0.5 mM to about 0 mM and for concentrations of HPBCD varying from about 0% (w/v) to about 6% (w/v); curve 1220 (stability 0.95) corresponds to concentrations of magnesium varying from about 0.8 mM to about 6 mM and for concentrations of HPBCD varying from about 0% (w/v) to about 8.5% (w/v); and curve 1230 (stability 0.90) corresponds to concentrations of magnesium varying from about 1.1 mM to about 6 mM and for concentrations of HPBCD varying from about 0% (w/v) to about 7.5% (w/v). From FIG. 12, it may be understood that as the concentration of magnesium increases, the concentration of HPBCD may be increased to maintain stability of the nucleotides above 0.9; and that for concentrations of HPBCD above about 7.5% (w/v) the stability of the nucleotides is relatively insensitive to the concentration of magnesium.

Figure 13:
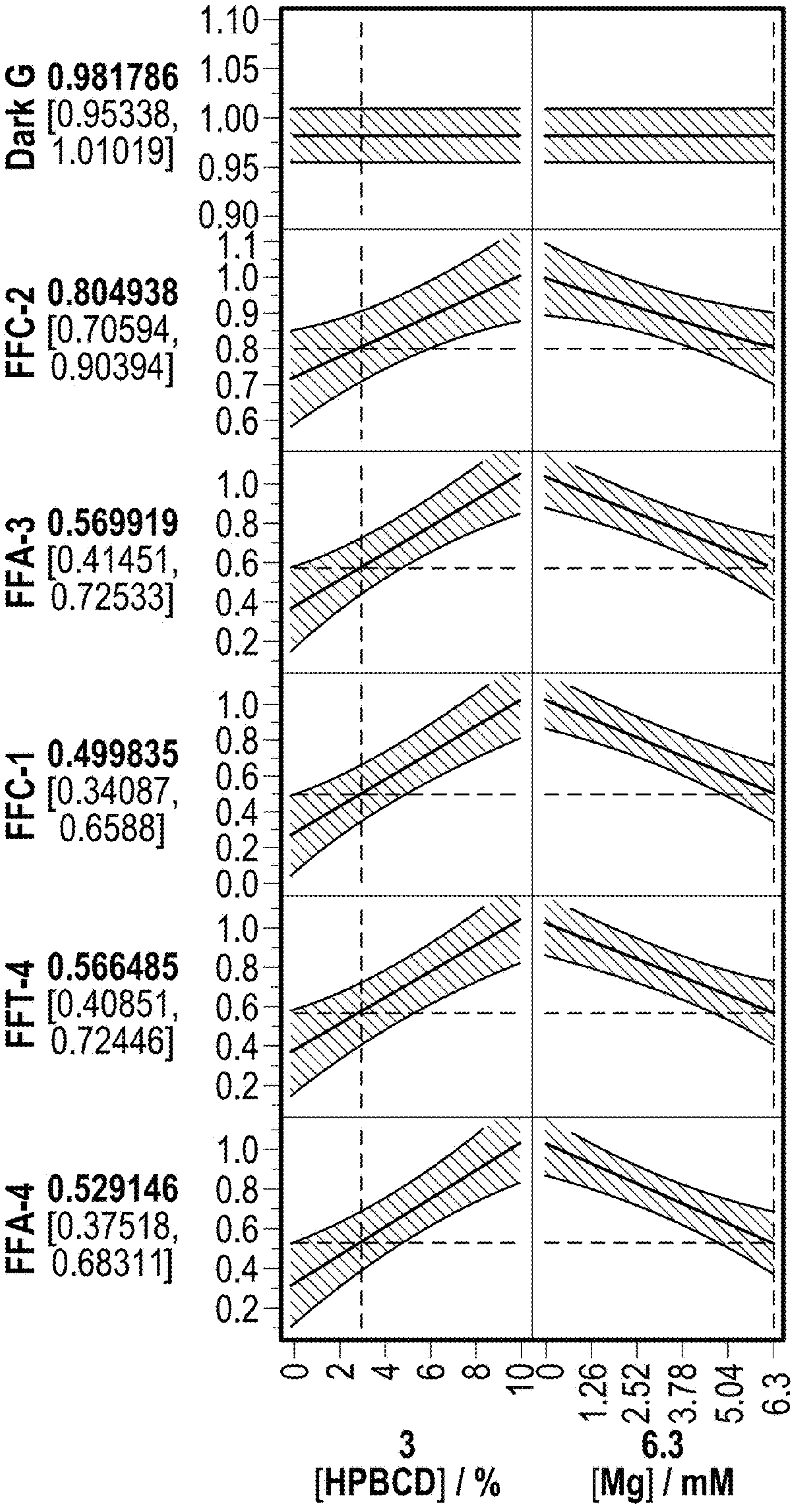
FIG. 13 includes plots of the stability of different fluorescently labeled nucleotides as a function of concentrations of the modified β-cyclodextrin HPBCD and of magnesium ions.

It was also observed that the stabilities of different nucleotides including different fluorescent dyes differed from one another, approximately as a function of the nucleotides' respective hydrophobicities, which were independently measured using the nucleotides' HPLC retention time. FIG. 13 includes plots of the stability of different fluorescently labeled nucleotides as a function of concentrations of the modified β-cyclodextrin HPBCD and of magnesium ions. The solutions used to prepare FIG. 13 included buffer components in the polishing solution, but did not include polymerase or an oligonucleotide template. In the left column of plots in FIG. 13, the concentration of magnesium ions was held at 6.3 mM while the concentration of HPBCD was varied between 0% and 10% (w/v), while in the right column of plots in FIG. 13, the concentration of HPBCD was held at 3% (w/v) while the concentration of magnesium ions was varied between 0 and 6.3 mM. The nucleotide referred to as "Dark G" in FIG. 13 included guanine (G) lacking a fluorescent dye, for use as a control, and may be seen to have a stability of about 0.98 that was relatively insensitive to concentration of HPBCD or magnesium ions. The nucleotide referred to as FFC-2, which included C coupled to dye "2", had a stability that increased from about 0.7 at 0% HPBCD and 6.3 mM magnesium ions, to about 1.0 at 10% (w/v) HPBCD and 6.3 mM magnesium ions, as shown in the left column of FIG. 13; and a stability that decreased from about 1.0 at 3% (w/v) HPBCD and 0 mM magnesium ions to about 0.8 at 3% (w/v) HPBCD and 6.3 mM magnesium ions, as shown in the right column of FIG. 13. The nucleotide referred to as FFA-3, which included adenine (A) coupled to dye "3", had a stability that increased from about 0.4 at 0% HPBCD and 6.3 mM magnesium ions, to about 1.0 at 10% (w/v) HPBCD and 6.3 mM magnesium ions, as shown in the left column of FIG. 13; and a stability that decreased from about 1.0 at 3% (w/v) HPBCD and 0 mM magnesium ions to about 0.6 at 3% (w/v) HPBCD and 6.3 mM magnesium ions, as shown in the right column of FIG. 13.

The nucleotide referred to as FFC-1, which included cytidine (C) coupled to dye "1", had a stability that increased from about 0.3 at 0% HPBCD and 6.3 mM magnesium ions, to about 1.0 at 10% (w/v) HPBCD and 6.3 mM magnesium ions, as shown in the left column of FIG. 13; and a stability that decreased from about 1.0 at 3% (w/v) HPBCD and 0 mM magnesium ions to about 0.5 at 3% (w/v) HPBCD and 6.3 mM magnesium ions, as shown in the right column of FIG. 13. The nucleotide referred to as FFT-4, which included thymine (T) coupled to dye "4", had a stability that increased from about 0.4 at 0% HPBCD and 6.3 mM magnesium ions, to about 1.0 at 10% (w/v) HPBCD and 6.3 mM magnesium ions, as shown in the left column of FIG. 13; and a stability that decreased from about 1.0 at 3% (w/v) HPBCD and 0 mM magnesium ions to about 0.6 at 3% (w/v) HPBCD and 6.3 mM magnesium ions, as shown in the right column of FIG. 13. The nucleotide referred to as FFA-1, which included adenine (A) coupled to dye "1", had a stability that increased from about 0.3 at 0% HPBCD and 6.3 mM magnesium ions, to about 1.0 at 10% (w/v) HPBCD and 6.3 mM magnesium ions, as shown in the left column of FIG. 13; and a stability that decreased from about 1.0 at 3% (w/v) HPBCD and 0 mM magnesium ions to about 0.5 at 3% (w/v) HPBCD and 6.3 mM magnesium ions, as shown in the right column of FIG. 13.

From FIG. 13, it may be understood that different nucleotides may have different stabilities than one another. For example, comparing the results for FFC-2 to those for FFA-3 and FFT-4, the nucleotides had different stabilities than one another at 0% (w/v) HPBCD and 6.3 mM magnesium ions: about 0.7 for FFC-2, and about 0.4 for FFA-3 and FFT-4, as shown in the left column of FIG. 13. The greater stability of FFC-2 as compared to FFA-3 and FFT-4 under these conditions was attributed to FFC-2 being less hydrophobic and less susceptible to aggregate formation in the presence of magnesium ions. Similarly, these nucleotides had different stabilities than one another at 3% (w/v) HPBCD and 6.3 mM magnesium ions: about 0.8 for FFC-2, and about 0.6 for FFA-3 and FFT-4. The greater stability of FFC-2 as compared to FFA-3 and FFT-4 under these conditions was attributed to FFC-2 being less hydrophobic and less susceptible to aggregate formation in the presence of magnesium ions. It also may be understood from FIG. 13 that at sufficient concentrations of HPBCD, e.g., greater than about 8% HPBCD, or greater than about 9% HPBCD, or greater than about 10% HPBCD, each of the nucleotides was stable regardless of the particular nucleobase used or the concentration of magnesium ions.

Additionally, comparing the results for FFC-2 to those for FFC-1, even though each of these nucleotides included the same nucleobase as one another, they had different stabilities than one another at 0% (w/v) HPBCD and 6.3 mM magnesium ions: about 0.7 for FFC-2, and about 0.3 for FFC-1, as shown in the left column of FIG. 13. The greater stability of FFC-2 as compared to FFC-1 under these conditions was attributed to FFC-2 being less hydrophobic and less susceptible to aggregate formation in the presence of magnesium ions. Similarly, these nucleotides had different stabilities than one another at 3% (w/v) HPBCD and 6.3 mM magnesium ions: about 0.8 for FFC-2, and about 0.5 for FFC-1. The greater stability of FFC-2 as compared to FFC-1 under these conditions was attributed to FFC-2 being less hydrophobic and less susceptible to aggregate formation in the presence of magnesium ions. Similarly, comparing the results for FFA-3 to those for FFA-1, even though each of these nucleotides included the same nucleobase as one another, they had different stabilities than one another at 0% (w/v) HPBCD and 6.3 mM magnesium ions: about 0.4 for FFA-3, and about 0.3 for FFA-1, as shown in the left column of FIG. 13. The greater stability of FFA-3 as compared to FFA-1 under these conditions was attributed to FFA-3 being less hydrophobic and less susceptible to aggregate formation in the presence of magnesium ions. Similarly, these nucleotides had different stabilities than one another at 3% (w/v) HPBCD and 6.3 mM magnesium ions: about 0.6 for FFA-3, and about 0.5 for FFA-1. The greater stability of FFA-3 as compared to FFA-1 under these conditions was attributed to FFA-3 being less hydrophobic and less susceptible to aggregate formation in the presence of magnesium ions. It also may be understood from FIG. 13 that at sufficient concentrations of HPBCD, e.g., greater than about 8% HPBCD, or greater than about 9% HPBCD, or greater than about 10% HPBCD, each of the nucleotides was stable regardless of the particular fluorescent dye used or the concentration of magnesium ions. It also may be understood from FIG. 13 that at sufficient concentrations of HPBCD, e.g., greater than about 8% HPBCD, or greater than about 9% HPBCD, or greater than about 10% HPBCD, each of the nucleotides was stable regardless of the particular fluorescent dye used or the concentration of magnesium ions.

Figure 14:
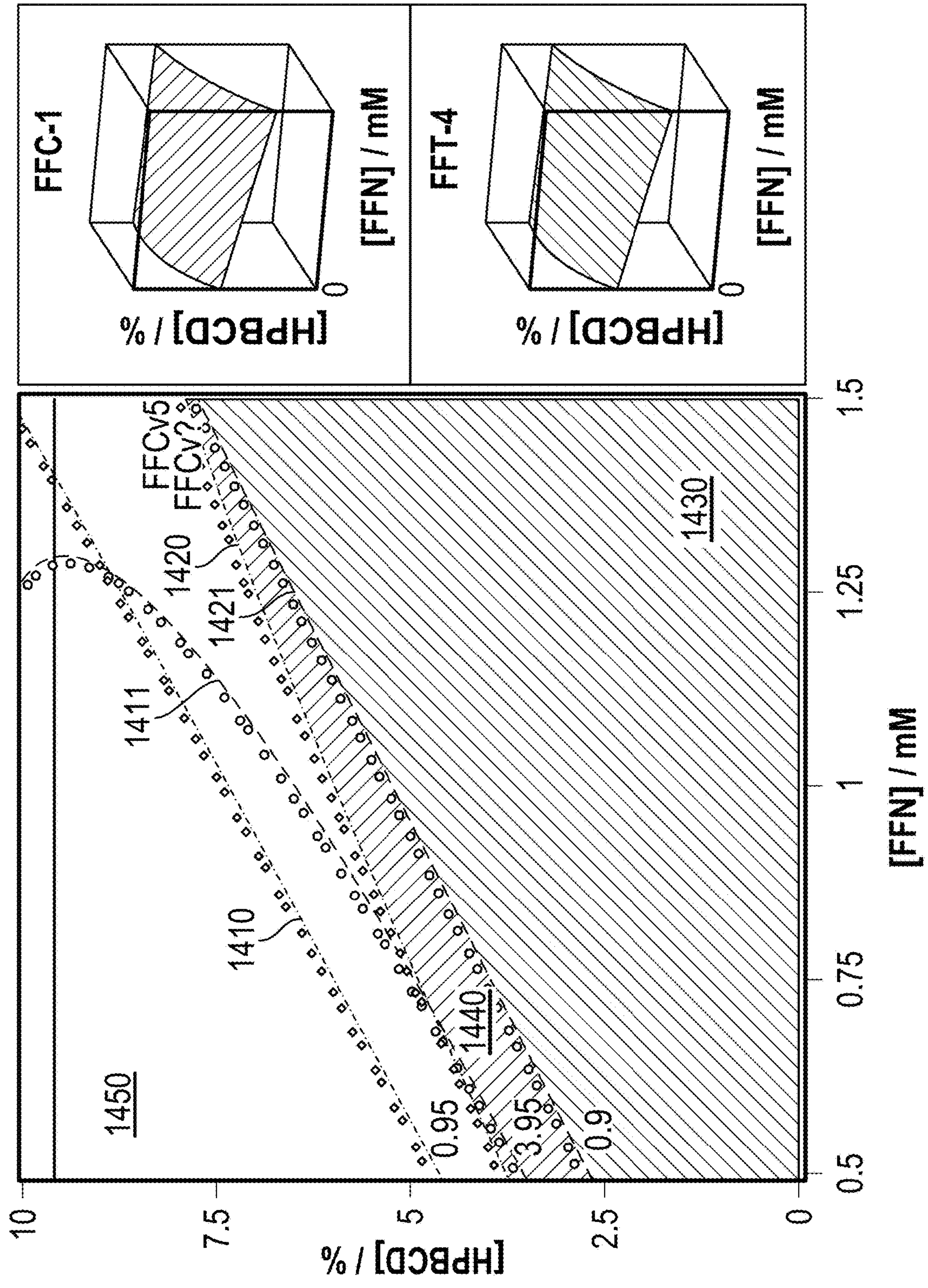
FIG. 14 is a contour plot of the stability of selected fluorescently labeled nucleotides as a function of concentrations of the modified β-cyclodextrin HPBCD and of those nucleotides.

As noted further above, the concentration of the nucleotides (FFNs) also may affect their solubility. FIG. 14 is a contour plot of the stability of selected fluorescently labeled nucleotides as a function of concentrations of the modified β-cyclodextrin HPBCD and of those nucleotides. The nucleotides used in FIG. 14 were FFC-1 and FFT-4, described above, and the concentration of magnesium ions was fixed at 6.3 mM. The solutions used to prepare FIG. 14 included buffer components in the polishing solution, as well as polymerase and an oligonucleotide template. Shaded region 1430 in FIG. 14 corresponds to combinations of nucleotide and HPBCD concentrations for which FFC-1 and FFT-4 are unstable (here, having a stability of less than about 0.90), while shaded region 1440 corresponds to combinations of nucleotide and HPBCD concentrations for which FFT-4 is stable (here, having a stability of about 0.9 to 1.0) and FFC-1 is unstable, and unshaded region 1450 corresponds to combinations of nucleotide and HPBCD concentrations for which both FFC-1 and FFT-4 are stable (here, having a stability of about 0.90 to 1.0), for 6.3 mM of magnesium ions. In FIG. 14, the curves 1410 and 1420 respectively correspond to ranges of concentrations of FFC-1 and of HPBCD that, together, provide a stability of FFC-1 of 0.95 and 0.9 for 6.3 mM of magnesium ions, and the curves 1411 and 1421 respectively correspond to ranges of concentrations of FFT-4 and of HPBCD that, together, provide a stability of FFT-4 of 0.95 and 0.9 for 6.3 mM of magnesium ions. It may be seen that curve 1410 (stability 0.95 of FFC-1) corresponds to concentrations of nucleotides varying from about 0.5 mM to about 1.4 mM and for concentrations of HPBCD varying from about 4.8% (w/v) to about 10% (w/v); curve 1420 (stability 0.90 of FFC-1) corresponds to concentrations of nucleotides varying from about 0.5 mM to about 1.5 mM and for concentrations of HPBCD varying from about 3.5% (w/v) to about 7.4% (w/v); curve 1411 (stability 0.95 of FFT-4) corresponds to concentrations of nucleotides varying from about 0.5 mM to about 1.3 mM and for concentrations of HPBCD varying from about 3.4% (w/v) to about 10% (w/v); and curve 1421 (stability 0.90 of FFT-4) corresponds to concentrations of nucleotides varying from about 0.5 mM to about 1.5 mM and for concentrations of HPBCD varying from about 2.6% (w/v) to about 7.3% (w/v). From FIG. 14, it may be understood that as the concentration of nucleotides increases, the concentration of HPBCD may be increased to maintain stability of the nucleotides, and that even for nucleotides having different hydrophobicities, a concentration of HPBCD may be used to suitably stabilize the nucleotides for a given concentration of magnesium. The insets of FIG. 14 illustrate normalized intensity responses of FFC-1 and FFT-4 shown as surface profiles, where the z-axis indicates the relative intensity as function of concentrations of HPBCD (y-axis) and concentrations of nucleotides (x-axis).

Figure 15:
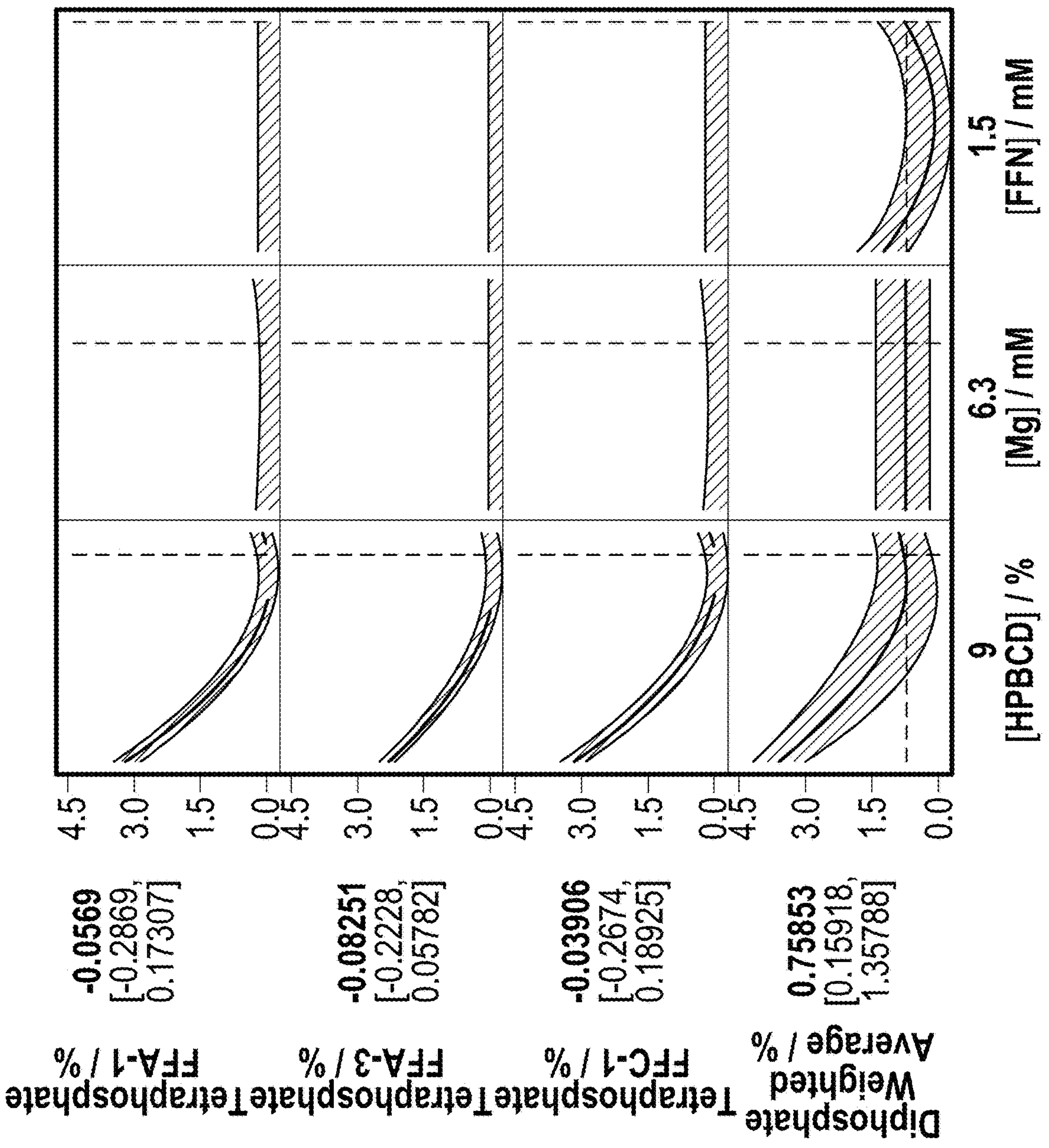
FIG. 15 includes plots of the concentrations of different byproducts as a function of concentrations of the modified β-cyclodextrin HPBCD, of magnesium ions, and of fluorescently labeled nucleotides.

It was found that HPBCD also suppressed the formation of different byproducts. FIG. 15 includes plots of the concentrations of different byproducts as a function of concentrations of the modified β-cyclodextrin HPBCD, of magnesium ions, and of the fluorescently labeled nucleotides FFA-1, FFA-3, and FFC-1. More specifically, the respective concentrations of diphosphate and tetraphosphate in the solutions were measured and used in the above-noted models. The solutions used to prepare FIG. 15 included buffer components in the polishing solution, as well as polymerase and an oligonucleotide template. In the left column of plots in FIG. 15, the concentration of magnesium ions was held at 6.3 mM and the concentration of nucleotides (FFNs) was held at 1.5 mM, while the concentration of HPBCD was varied between 0% and 10% (w/v); in the middle column of plots in FIG. 15, the concentration of HPBCD was held at 9% (w/v) and the concentration of nucleotides (FFNs) was held at 1.5 mM, while the concentration of magnesium ions was varied between 0 mM and 7.8 mM; and in the right column of plots in FIG. 15, the concentration of HPBCD was held at 9% (w/v) and the concentration of magnesium ions was held at 6.3 mM, while the concentration of nucleotides was varied between 0.5 and 1.5 mM.

From the left-most column of FIG. 15, it may be seen that for 0% (w/v) HPBCD, the FFA-1 solution had a concentration of about 3.0% (w/v) tetraphosphate relative to the nucleotide, and the concentration of tetraphosphate decreased smoothly as the concentration of HPBCD increased; similarly, for 0% (w/v) HPBCD, the FFA-3 solution had a concentration of about 2.5% (w/v) tetraphosphate relative to the nucleotide, and the concentration of tetraphosphate decreased smoothly as the concentration of HPBCD increased; similarly, for 0% (w/v) HPBCD, the FFC-1 solution had a concentration of about 3.8% (w/v) tetraphosphate relative to the nucleotide, and the concentration of tetraphosphate decreased smoothly as the concentration of HPBCD increased; and for 0% (w/v) HPBCD, the weighted average concentration of diphosphate was about 3.8% (w/v), and the concentration of diphosphate decreased smoothly as the concentration of HPBCD increased. From the middle column of plots in FIG. 15, it may be seen that for 9% HPBCD and 1.5 mM nucleotides, the FFA-1 solution, the FFA-3 solution, and the FFC-1 solution each had about zero tetraphosphate for any concentration of magnesium ions, and the weighted average concentration of diphosphate was about 0.75% (w/w). From the right column of plots in FIG. 15, it may be seen that for 9% HPBCD and 6.3 mM magnesium ions, the FFA-1 solution, the FFA-3 solution, and the FFC-1 solution each had about zero tetraphosphate for any concentration of nucleotides, and the weighted average concentration of diphosphate varied between about 1.5% (w/w) and about 0.3% (w/w).

Accordingly, it may be understood that appropriately selecting the concentration of various solution components, such as modified α-cyclodextrins, modified β-cyclodextrins, or modified γ-cyclodextrins, may facilitate polishing and sequencing of nucleotides, for example by improving solubility of the nucleotides and/or by inhibiting generation of byproducts such as tetraphosphate or diphosphate, and thus may enhance the accuracy of the sequencing.

ADDITIONAL COMMENTS

While various illustrative examples are described above, it will be apparent to one skilled in the art that various changes and modifications may be made therein without departing from the invention. For example, although it has been found that thermostable polymerases may be particularly useful in purifying 3'-blocked nucleotides, it should be appreciated that any suitable polymerase that selectively polymerizes 3'-OH nucleotides relative to 3'-blocked nucleotides may be used. The appended claims are intended to cover all such changes and modifications that fall within the true spirit and scope of the invention.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

What is claimed is:

1. A method for purifying nucleotides, the method comprising:

preparing a solution comprising (a) 3'-blocked nucleotides, (b) 3'-OH nucleotides, (c) a polishing polymerase, and (d) a template, wherein the 3'-blocked nucleotides are coupled to a blocking group which inhibits polymerization;

using the polishing polymerase and the template to selectively polymerize the 3'-OH nucleotides and thus reduce a concentration in the solution of the 3'-OH nucleotides relative to the 3'-blocked nucleotides.

2. The method of claim 1, wherein each of the 3'-blocked nucleotides includes a detectable moiety.

3. The method of claim 1, wherein preparing the solution comprises adding water, the polishing polymerase, and the template to a lyophilized mixture of the 3'-blocked nucleotides and the 3'-OH nucleotides.

4. The method of claim 1, wherein preparing the solution comprises adding water to a lyophilized mixture of the 3'-blocked nucleotides, the 3'-OH nucleotides, the polishing polymerase, and the template.

5. The method of claim 1, wherein the polishing polymerase comprises a thermostable polymerase.

6. The method of claim 5, wherein the thermostable polymerase is selected from the group consisting of: *Pyrococcus* sp. (strain GB-D) DNA polymerase, Taq, Bst, *Sulfolobus* DNA Polymerase IV, and Pfu.

7. The method of claim 5, further comprising heating the solution while using the thermostable polymerase and the template.

8. The method of claim 7, wherein the solution is heated to a temperature of about 30-75° C.

9. The method of claim 7, wherein the solution is heated to a temperature of about 40-60° C.

10. The method of claim 7, wherein heating the solution comprises flowing the solution through a cache manifold comprising a heat exchanger with inner and outer sleeves, one or both of which may be heated; and a coiled fluidic pathway that is located between the sleeves through which the solution flows, thereby heating the solution.

11. The method of claim 10, wherein the inner structure comprises an inner sleeve through which a fluid flows.

12. The method of claim 1, wherein the solution further comprises yeast inorganic pyrophosphatase (YPP) to increase a rate at which 3'-OH nucleotides are polymerized as compared to such rate in the absence of YPP.

13. The method of claim 1, wherein the polishing polymerase and the template are used in a sequencing-by-synthesis instrument.

14. The method of claim 1, wherein the solution further comprises a modified α-cyclodextrin, a modified β-cyclodextrin, or a modified γ-cyclodextrin.

15. The method of claim 14, wherein the modified a-cyclodextrin is (2-hydroxypropyl)-α-cyclodextrin, the modified β-cyclodextrin is (2-hydroxypropyl)-β-cyclodextrin (HPBCD) or (2-hydroxyethyl)-β-cyclodextrin (HEBCD), or the modified γ-cyclodextrin is (2-hydroxypropyl)-γ-cyclodextrin.

16. The method of claim 14, wherein each of the 3'-blocked nucleotides is coupled to a fluorescent dye, and wherein the modified α-cyclodextrin, modified β-cyclodextrin, or modified γ-cyclodextrin promotes solubility of the fluorescent dye.

17. The method of claim 14, wherein the modified α-cyclodextrin, modified β-cyclodextrin, or modified γ-cyclodextrin has a concentration in the solution of about 1% to about 10% (weight/volume).

18. The method of claim 14, wherein the 3'-blocked nucleotides have a concentration in the solution of less than about 1.5 mM.

19. The method of claim 14, wherein the solution further comprises magnesium ions at a concentration of at least about 1 mM.

20. The method of claim 14, wherein the modified α-cyclodextrin, modified β-cyclodextrin, or modified γ-cyclodextrin inhibits formation of diphosphate in the solution.

21. The method of claim 14, wherein the modified α-cyclodextrin, modified β-cyclodextrin, or modified γ-cyclodextrin inhibits formation of tetraphosphate in the solution.

22. The method of claim 1, wherein the blocking group is selected from azidomethyl, acetal, and thiocarbamate.

* * * * *

SEQUENCE LISTING

```
<160> NUMBER OF SEQ ID NOS: 12

<210> SEQ ID NO 1
<211> LENGTH: 66
<212> TYPE: DNA
<213> ORGANISM: Artificial Sequence
<220> FEATURE:
<223> OTHER INFORMATION: illustrative example of primer 141, loop
      oligonucleotide 142, complementary primer 151, and fourth portion
      152
<220> FEATURE:
<221> NAME/KEY: misc_feature
<222> LOCATION: (1)..(20)
<223> OTHER INFORMATION: degenerated bases, n = a, c, g, or t

<400> SEQUENCE: 1

nnnnnnnnnn nnnnnnnnnn cggccatata actggtagct tttttaagct accagttata     60

tggccg                                                                66


<210> SEQ ID NO 2
<211> LENGTH: 20
<212> TYPE: DNA
<213> ORGANISM: Artificial Sequence
<220> FEATURE:
<223> OTHER INFORMATION: illustrative example of primer 141

<400> SEQUENCE: 2

aagctaccag ttatatggcc                                                 20


<210> SEQ ID NO 3
<211> LENGTH: 21
<212> TYPE: DNA
<213> ORGANISM: Artificial Sequence
<220> FEATURE:
<223> OTHER INFORMATION: illustrative example of complementary primer
      151

<400> SEQUENCE: 3

cggccatata actggtagct t                                               21


<210> SEQ ID NO 4
<211> LENGTH: 20
<212> TYPE: DNA
<213> ORGANISM: Artificial Sequence
<220> FEATURE:
<223> OTHER INFORMATION: illustrative example of fourth position 152
<220> FEATURE:
<221> NAME/KEY: misc_feature
<222> LOCATION: (1)..(20)
<223> OTHER INFORMATION: degenerated bases, n = a, c, g, or t
```

<400> SEQUENCE: 4
nnnnnnnnnn nnnnnnnnnn 20

<210> SEQ ID NO 5
<211> LENGTH: 41
<212> TYPE: DNA
<213> ORGANISM: Artificial Sequence
<220> FEATURE:
<223> OTHER INFORMATION: template sequence
<220> FEATURE:
<221> NAME/KEY: misc_feature
<222> LOCATION: (1)..(20)
<223> OTHER INFORMATION: degenerated bases, n = a, c, g, or t

<400> SEQUENCE: 5
nnnnnnnnnn nnnnnnnnnn cggccatata actggtagct t 41

<210> SEQ ID NO 6
<211> LENGTH: 21
<212> TYPE: DNA
<213> ORGANISM: Artificial Sequence
<220> FEATURE:
<223> OTHER INFORMATION: primer oligonucleotide sequence

<400> SEQUENCE: 6
aagctaccag ttatatggcc g 21

<210> SEQ ID NO 7
<211> LENGTH: 25
<212> TYPE: DNA
<213> ORGANISM: Artificial Sequence
<220> FEATURE:
<223> OTHER INFORMATION: template sequence
<220> FEATURE:
<221> NAME/KEY: misc_feature
<222> LOCATION: (1)..(4)
<223> OTHER INFORMATION: degenerated bases, n = a, c, g, or t

<400> SEQUENCE: 7
nnnncggcca tataactggt agctt 25

<210> SEQ ID NO 8
<211> LENGTH: 27
<212> TYPE: DNA
<213> ORGANISM: Artificial Sequence
<220> FEATURE:
<223> OTHER INFORMATION: template sequence
<220> FEATURE:
<221> NAME/KEY: misc_feature
<222> LOCATION: (1)..(6)
<223> OTHER INFORMATION: degenerated bases, n = a, c, g, or t

<400> SEQUENCE: 8
nnnnnncggc catataactg gtagctt 27

<210> SEQ ID NO 9
<211> LENGTH: 47
<212> TYPE: DNA
<213> ORGANISM: Artificial Sequence
<220> FEATURE:
<223> OTHER INFORMATION: hairpin G template

<400> SEQUENCE: 9
gggggggggg ggcggccata taactggtca ctccagttat atggccg 47

<210> SEQ ID NO 10

-continued

```
<211> LENGTH: 47
<212> TYPE: DNA
<213> ORGANISM: Artificial Sequence
<220> FEATURE:
<223> OTHER INFORMATION: hairpin T template

<400> SEQUENCE: 10

tttttttttt ttcggccata taactggtca ctccagttat atggccg                  47


<210> SEQ ID NO 11
<211> LENGTH: 47
<212> TYPE: DNA
<213> ORGANISM: Artificial Sequence
<220> FEATURE:
<223> OTHER INFORMATION: hairpin C template

<400> SEQUENCE: 11

cccccccccc cccggccata taactggtca ctccagttat atggccg                  47


<210> SEQ ID NO 12
<211> LENGTH: 47
<212> TYPE: DNA
<213> ORGANISM: Artificial Sequence
<220> FEATURE:
<223> OTHER INFORMATION: hairpin A template

<400> SEQUENCE: 12

aaaaaaaaaa aacggccata taactggtca ctccagttat atggccg                  47
```